(12) United States Patent
Paulsen et al.

(10) Patent No.: US 9,616,105 B2
(45) Date of Patent: Apr. 11, 2017

(54) AGENT FOR THE TREATMENT AND/OR PROPHYLAXIS OF AN AUTOIMMUNE DISEASE AND FOR THE FORMATION OF REGULATORY T CELLS

(71) Applicant: AiCuris GmbH & Co. KG, Wuppertal (DE)

(72) Inventors: Daniela Paulsen, Wuppertal (DE); Nina Brunner, Essen (DE); Dorothy Bray, Buckinghamshire (GB)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 14/752,726

(22) Filed: Jun. 26, 2015

(65) Prior Publication Data

US 2015/0374788 A1 Dec. 31, 2015

Related U.S. Application Data

(63) Continuation of application No. 12/941,885, filed on Nov. 8, 2010, now abandoned, which is a continuation of application No. PCT/EP2009/003076, filed on Apr. 28, 2009.

(30) Foreign Application Priority Data

May 8, 2008 (DE) .................. 10 2008 023 820

(51) Int. Cl.
| | |
|---|---|
| A61K 38/00 | (2006.01) |
| C07K 14/47 | (2006.01) |
| A61K 38/16 | (2006.01) |
| A61K 38/20 | (2006.01) |
| A61K 35/17 | (2015.01) |
| A61K 45/06 | (2006.01) |

(52) U.S. Cl.
CPC .......... *A61K 38/2013* (2013.01); *A61K 35/17* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,348,192 B1 | 2/2002 | Chan et al. | |
| 6,927,043 B2 * | 8/2005 | Chan ...................... | C07K 14/55 435/320.1 |
| 2002/0164300 A1 | 11/2002 | Chan et al. | |
| 2004/0175357 A1 | 9/2004 | Shanafelt et al. | |
| 2006/0189520 A1 * | 8/2006 | Brand .................... | A61K 38/26 424/85.1 |
| 2007/0036752 A1 | 2/2007 | Gillies et al. | |
| 2011/0150826 A1 | 6/2011 | Paulsen et al. | |

FOREIGN PATENT DOCUMENTS

| | | | |
|---|---|---|---|
| DE | 20 2005 001 888 | 7/2005 | |
| EP | 2288372 B1 | 3/2011 | |
| WO | WO 99/60128 | * 11/1999 | ............. C12N 15/26 |
| WO | WO-99/60128 | 11/1999 | |
| WO | WO-02/00243 | 1/2002 | |
| WO | WO-03/015697 | 2/2003 | |
| WO | WO-2009/061853 | 5/2009 | |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Q6QWN0 (submitted by Chikara et al. integrated in UniProtKB, Jul. 5, 2004).*
Liston et al. 2007. Immunology and Cell Biol. 85:338-342.*
Adeegbe et al., "Cutting edge: allogeneic CD4+CD25+Foxp3+ T regulatory cells suppress autoimmunity while establishing transplantation tolerance," J Immunol (2006) 176(12):7149-7153.
Ahmadzadeh et al., "IL-2 administration increases CD4+ CD25(hi) Foxp3+ regulatory T cells in cancer patients," Blood (2006) 107(6):2409-2414.
Aicuris GmbH & Co. KG, "IL-2 mutein: highly specific T reg cell activation for treatment of autoimmunity," Non-confidential presentation (2016) 13 pages.
Antony et al., "CD4+CD25+ T regulatory cells, immunotherapy of cancer, and interleukin-2," J Immunother (2005) 28(2):120-128.
Baker et al., "Gene therapy in autoimmune, demyelinating disease of the central nervous system," Gene Therapy (2003) 10:844-853.
Bayer et al., "Function of the IL-2R for Thymic and Peripheral CD4+CD25+Foxp3+ T Regulatory Cells," The Journal of Immunology (2007) 178:4062-4071.
Bresson et al., "Anti-CD3 and nasal proinsulin combination therapy enhances remission from recent-onset autoimmune diabetes by inducing Tregs," The Journal of Clinical Investigation (2006) 116(5):1371-1381.
Burchill et al., "Interleukin-2 receptor signaling in regulatory T cell development and homeostasis," Immunology Letters (2007) 114:1-8.
Bowie et al., "Deciphering the Message in Protein Sequences: Tolerance to Amino Acid Substitutions," Science (1990) 247:1306-1310.
Cassell et al., "Therapeutic enhancement of IL-2 through molecular design," Current Pharmaceutical Design (2002) 8:2171-2183.
Chatila TA., "Role of regulatory T cells in human diseases," J Allergy Clin Immunol (2005) 116(5):949-959.
Chianese-Bullock et al., "Autoimmune toxicities associated with the administration of antitumor vaccines and low-dose interleukin-2," J Immunother (2005) 28(4):412-419.

(Continued)

*Primary Examiner* — Shulamith H Shafer
(74) *Attorney, Agent, or Firm* — Morrison & Foerster LLP

(57) ABSTRACT

The present invention relates to an agent for the treatment and/or prophylaxis of an autoimmune disease, an agent for the formation of regulatory T cells ($T_{Reg}$) in an organism and various methods in which the agents according to the invention are used.

15 Claims, 10 Drawing Sheets

(56) References Cited

OTHER PUBLICATIONS

Cohen et al., "CD4(+)CD25(+) immunoregulatory T Cells: new therapeutics for graft-versus-host disease," J Exp Med (2002) 196(3):401-406.
Dejaco et al., "Imbalance of regulatory T cells in human autoimmune diseases," Immunology (2005) 117:289-300.
Ehrenstein et al., "Compromised function of regulatory T cells in rheumatoid arthritis and reversal by anti-TNFalpha therapy," J Exp Med (2004) 200(3):277-285.
Frantz, "In vivo we trust," Nature Reviews (2003) 2:501.
Fujita et al., "Structure of the human interleukin 2 gene," Proc Natl Acad Sci U.S.A. (1983) 80(24):7437-7441.
Haegele et al., "Increase of CD8+ T-effector memory cells in peripheral blood of patients with relapsing-remitting multiple sclerosis compared to healthy controls," J Neuroimmunol (2007) 183(1-2):168-174.
Ju et al., "Structure-function analysis of human interleukin-2," J Biol Chem (1987) 262(12):5723-5731.
Kukreja et al., "Multiple immune-regulatory defects in type-1 diabetes," J Clin Invest (2002) 109:131-140.
Knoechel et al., "Sequential development of interleukin 2-dependent effector and regulatory T cells in response to endogenous systemic antigen," J Exp Med (2005) 202(10):1375-1386.
Kroemer et al., "The role of interleukin 2 in autoimmunity," Immunology Today (1989) 10(7):246-251.
Lan et al., "Regulatory T cells: development, function and role in autoimmunity," Autoimmun Rev (2005) 4(6):351-363.
Liang et al., "Studies of structure-activity relationships of human interleukin-2*," J Biol Chem (1986) 261(1):334-337.
Liu et al., "Increased CD8+ central memory T cells in patients with multiple sclerosis," Mult Scler (2007) 13(2):149-155.
Malek et al., "CD4 regulatory T cells prevent lethal autoimmunity in IL-2RB-deficient mice: implications for the nonredundant function of IL-2," Immunity (2002) 17(2):167-178.
Malek et al, "Tolerance, not immunity, crucially depends on IL-2," Immunology (2004) 4:665-674.
Margolin et al., "Phase I trial of BAY 50-4798, an Interleukin-2-specific agonist in advanced melanoma and renal cancer," Clin Cancer Res (2007) 13(11):3312-3319.
Matthews et al., "BYA 50-4798, a novel, high-affinity receptor-specific recombinant interleukin-2 analog, induces dose-dependent increases in CD25 expression and proliferation among unstimulated, human peripheral blood mononuclear cells in vitro," Clinical Immunology (2004) 113(3):248-255.
MedlinePlus Encyclopedia, http://www.nlm.nih.gov/medlineplus/ency/article/000816.htm, updated May 29, 2011, downloaded Aug. 30, 2011.
Moschos et al., "Focus on FOCIS: interleukin 2 treatment associated autoimmunity," Clin Immunol (2008) 127(2):123-129.
Nadkarni et al., "Anti-TNF-alpha therapy induces a distinct regulatory T cell population in patients with rheumatoid arthritis via TGF-beta," J Exp Med (2007) 204(1):33-39.
Nelson, "Interleukin-2 signaling and the maintenance of self-tolerance," Curr Dir Autoimmun (2002) 5:92-112.
Ngo et al., "Computational complexity, protein structure prediction, and the Levinthal paradox," The Protein Folding Problem and Tertiary Structure Prediction (1994) pp. 432-506.
Nishimura et al., "Induction of antigen-specific immunologic tolerance by in vivo and in vitro antigen-specific expansion of naturally arising Foxp3+CD25+CD4+ regulatory T cells," International Immunology (2004) 16(8):1189-1201.
Oda et al., "Genetic polymorphism in FOXP3 gene: imbalance in regulatory T-cell role and development of human diseases," J Genet (2013) 92(1):163-171.
Pandiyan et al., "The control of CD4+CD25+Foxp3+ regulatory T cell survival," Biology Direct (2008) 3:6 1-12.
Pettit et al., "The development of site-specific drug delivery systems for protein and peptide biopharmaceuticals," Trends in Biotech (1998) 16:343-349.
Pfortner, "Molecular Characterization of Human Regulatory T Cell in Health and Disease," Technical University Carolo-Wilhelmina in Braunschweig (2007) pp. 1-22, 115-119.
Powell et al., "Inability to mediate prolonged reduction of regulatory T Cells after transfer of autologous CD25-depleted PBMC and interleukin-2 after lymphodepleting chemotherapy," J Immunother (2007) 30(4):438-447.
Q6QWN0, submitted by Chikara et al. integrated in UniProtKB, Jul. 5, 2004.
Rao et al., "Interleukin-2 mutants with enhanced alpha-receptor subunit binding affinity," Protein Eng (2003) 16(12):1081-1087.
Robb et al., "Amino acid sequence and post-translational modification of human interleukin 2," Proc Natl Acad Sci USA (1984) 81:6486-6490.
Sakaguchi et al., "Naturally arising CD4+ regulatory t cells for immunologic self-tolerance and negative control of immune responses," Annu Rev Immunol (2004) 22:531-562.
Setoguchi et al., "Homeostatic maintenance of natural Foxp3(+) CD25(+) CD4(+) regulatory T cells by interleukin (IL)-2 and induction of autoimmune disease by IL-2 neutralization," J. Exp. Med. (2005) 201(5):723-735.
Shanafelt et al., "A T-cell-selective interleukin 2 mutein exhibits potent antitumor activity and is well tolerated in vivo," Nat Biotechnol (2000) 18(11):1197-1202.
Solomou et al., "Molecular basis of deficient IL-2 production in T cells from patients with Systemic Lupus Erythematosus," J Immunol (2001) 166:4216-4222.
Sugimoto et al., "Foxp3-dependent and -independent molecules specific for CD25+CD4+ natural regulatory T cells revealed by DNA microarray analysis," Int Immunol (2006) 18(8):1197-1209.
Tang et al., "In Vitro-expanded antigen-specific regulatory T cells suppress autoimmune diabetes," J Exp Med (2004) 199(11):1455-1465.
Thornton et al., "Activation requirements for the induction of CD4+CD25+ T cells suppressor function," Eur J Immunol (2004) 34(2):366-376.
Van Der Vliet et al., "Effects of the administration of high-dose interleukin-2 on immunoregulatory cell subsets in patients with advanced melanoma and renal cell cancer," Clin Cancer Res (2007)13(7):2100-2108.
Vandenbark et al., "Anti-TNF-alpha therapy induces a distinct regulatory T cell population in patients with rheumatoid arthritis via TGF-beta," Immunology (2008) 123(1):66-78.
Wandinger et al., "Diminished production of type-I interferons and interleukin-2 in patients with multiple sclerosis," Journal of Neurological Sciences (1997) 149:87-93.
Wang et al., "Site-specific mutagenesis of the human interleukin-2 gene: structure-function analysis of the cysteine residues," Science 224:1431-1433.
Wells, "Additivity of mutational effects in proteins," Biochemistry (1990) 29(37):8509-8517.
Yagi et al., "Crucial role of FOXP3 in the development and function of human CD25+CD4+ regulatory T cells," International Immunology (2004) 16(11):1643-1656.
Restriction Requirement for U.S. Appl. No. 12/941,885, mailed on Jun. 8, 2011, 8 pages.
Response to Restriction Requirement for U.S. Appl. No. 12/941,885, filed Jul. 8, 2011, 7 pages.
Office Action for U.S. Appl. No. 12/941,885, mailed Sep. 13, 2011, 18 pages.
Response to Office Action for U.S. Appl. No. 12/941,885, filed Mar. 13, 2012, 38 pages.
Office Action for U.S. Appl. No. 12/941,885, mailed Jul. 26, 2012, 15 pages.
Request for Continued Examination for U.S. Appl. No. 12/941,885, filed Jan. 25, 2013, 12 pages.
Notice to the applicant regarding a non-compliant or non-responsive amendment for U.S. Appl. No. 12/941,885, mailed Oct. 8, 2014, 3 pages.
Response to Notice to the applicant regarding a non-compliant or non-responsive amendment for U.S. Appl. No. 12/941,885, filed Dec. 8, 2014, 7 pages.

(56) References Cited

OTHER PUBLICATIONS

Office Action for U.S. Appl. No. 12/941,885, mailed Jan. 27, 2015, 13 pages.
Restriction Requirement for U.S. Appl. No. 14/752,726, mailed Dec. 10, 2015, 6 pages.
Response to Restriction Requirement for U.S. Appl. No. 14/752,726, filed Feb. 10, 2016, 7 pages.
Office Action for U.S. Appl. No. 14/752,726, mailed Apr. 15, 2016, 20 pages.

* cited by examiner

SEQUENCE LISTING

<160> NUMBER OF SEQ ID NOS: 3

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

```
Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                   70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Cys Gln Ser Ile
         115                 120                 125

Ile Ser Thr Leu Thr
        130

<210> SEQ ID NO 2
<211> LENGTH: 465
<212> TYPE: DNA
<213> ORGANISM: Homo sapiens

<400> SEQUENCE: 2
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactt gataa                    465

<210> SEQ ID NO 3
<211> LENGTH: 133
<212> TYPE: PRT
<213> ORGANISM: Artificial Sequence
<220> FEATURE:
<223> OTHER INFORMATION: synthetically constructed hIL-2-N88R mutein

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                   70                  75                  80

Arg Pro Arg Asp Leu Ile Ser Arg Ile Asn Val Ile Val Leu Glu Leu
                 85                  90                  95
```

```
Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Gln Ser Ile
        115                 120                 125

Ile Ser Thr Leu Thr
    130
```

AGENT FOR THE TREATMENT AND/OR PROPHYLAXIS OF AN AUTOIMMUNE DISEASE AND FOR THE FORMATION OF REGULATORY T CELLS

CROSS-REFERENCES TO RELATED APPLICATIONS

This application is a continuation of U.S. Ser. No. 12/941,885, filed on Nov. 8, 2010, currently pending, which is a continuation of International Patent Application PCT/EP2009/003076 filed on Apr. 28, 2009 and designating the United States, which was not published under PCT Article 21(2) in English, and claims priority of German Patent Application DE 10 2008 023 820.1 filed on May 8, 2008. The contents of these prior applications are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 595282000702SeqList.txt, date recorded: Sep. 4, 2015, size: 3,501 bytes)

BACKGROUND OF THE INVENTION

Field of the Invention

The present invention relates to an agent for the treatment and/or prophylaxis of an autoimmune disease, an agent for the formation of regulatory T cells ($T_{Reg}$) in an organism and various methods in which the agents according to the invention are used.

Related Prior Art

Autoimmune diseases are characterized by an excessive reaction of the immune system against endogenous tissue. The immune system erroneously recognizes endogenous tissue as foreign bodies to be combated. This results in severe inflammatory reactions, which lead to damage to organs affected by them.

An important part in distinguishing between endogenous and exogenous structures is played by T lymphocytes or T cells, which are "trained" in the thymus to dock only onto endogenous cell surface molecules, the so-called MHC molecules, and thus to tolerate endogenous structures. These processes are called "clonal deletion" and "clonal selection". During the initial selection in the thymus, only those T cells, which are able to recognize MHC molecules on the endogenous cell membranes survive, while the binding is however not so strong that it could lead to activation of the T cells. T cells which cannot bind to or recognize endogenous MHC molecules at all are eliminated. In the clonal deletion also taking place in the thymus, those T cells which are able to "unerringly" recognize and strongly bind endogenous MHC molecules in such a manner that they would be activated, which would in the end lead to the destruction of endogenous cells, are eliminated. This process is one of those measures which the immune system takes in order to be able to protect the "self" and combat the "exogenous".

In autoimmune diseases, a group of the T cells behaves abnormally. In addition to the still functioning defence from exogenous molecules and organisms, they now also attack endogenous structure. Organs or tissues are perceived as exogenous. There can be various consequences: if vital structures are affected, an autoimmune disease will take a fatal course. The immune system directs its defence against these structures, cellular and also humoral defence reactions are set in motion, and autoantibodies are formed, as a result of which the organs affected in the course of time cease to function. Most commonly, the immune system is weakened and the body becomes susceptible to all kinds of diseases. Under some circumstances, recognition of the exogenous is also disrupted, and as a result the spreading of degenerated cancer cells can no longer be effectively prevented, and those affected are more susceptible to infectious diseases. In the course of the disease, cells of the immune system destroy the endogenous structures, while the body's repair mechanisms attempt as far as possible to regenerate the damaged organ parts. As a rule, without treatment this erroneous attack of the defensive system continues throughout life or until the complete destruction of the target structure.

In spite of intensive research, the exact causes of autoimmune diseases are still unclear. Accepted hypotheses are based on the assumption that autoimmune diseases are acquired through a genetic predisposition, e.g., owing to the presence of certain MHC molecule types, in combination with external influences. If such genetically determined factors are present in the body of the person affected, and in addition unfavourable environmental factors such as severe stress, infections, pregnancy, etc., occur, this can lead to the onset of autoimmune diseases.

The immune system consists of various cells which are capable of combating infectious agents which have invaded the body. The mechanism of the immune response includes the activation of specialized cells and the acquisition of effector functions, such as the cytotoxicity of certain T cells, which express the so-called CD8 transmembrane glycoprotein and which are therefore described as $CD8^+T$ cells.

Regulatory T cells ($T_{Reg}$), previously also described as suppressor T cells, are a specialized subgroup of the T cells. They have the function of suppressing the activation of the immune system and thereby regulating the self-tolerance of the immune system. As a result, in the healthy organism they prevent the onset of autoimmune diseases. Various $T_{Reg}$ populations have been described, including those which express the proteins CD4, CD25 and Foxp3 and are therefore described as $CD4^+CD25^+Foxp3^+$ T cells. In addition, $T_{Reg}$ have been described which do express CD4 and Foxp3, but not CD25, so-called $CD4^+CD25^-Foxp3^+$ T cells.

Lan et al. (2005), Regulatory T cells: development, function and role in autoimmunity, Autoimmun Rev. 4(6), p. 351 to 363, describe a murine model in which the depletion of $CD4^+CD25^+$ regulatory T cells leads to the spontaneous development of autoimmune diseases.

Chatila T. A. (2005), Role of regulatory T cells in human diseases, 116(5), p. 949 to 959, report that a congenital deficiency of $CD4^+CD25^+$ regulatory T cells due to a mutation in the gene which codes for the protein Foxp3 contributes to the development of autoimmune diseases.

There is a review concerning regulatory T cells in the journal "Nature Immunology", which was published in March 2005.

Autoimmune diseases are treated according to the organ affected. In this, the basic principle of the causal therapy is to suppress the activity of the immune system by administration of immunosuppressants, e.g., cortisone. These substances are characterized by multiple systemic side-effects and interactions, owing to which attempts have been made to develop new drugs which specifically influence the mechanisms involved in the disease event. Examples of this are natalizumab and infliximab. Natalizumab is a monoclonal antibody and selective inhibitor of IgG4, an adhesion molecule which is located on the surface of white blood cells. Natalizumab inhibits the migration of white blood cells into inflammation foci and is used for the treatment of particularly aggressive forms of plaque progressive multiple sclerosis. Infliximab is a chimeric monoclonal antibody against tumour necrosis factor α (TNFα), which plays a key part in autoimmune inflammatory reactions. Infliximab is used in rheumatoid arthritis, Crohn's disease, Bechterew disease and psoriasis.

In Ehrenstein et al. (2004), Compromised function of regulatory T cells in rheumatoid arthritis and reversal by anti-TNFα therapy, J. Exp. Med., Vol. 200, No. 3, p. 277-285, it is reported that, as a monoclonal antibody directed against TNFα, infliximab can improve the therapy of rheumatoid arthritis.

A similar suggestion is made by Nadkarni et al. (2007), Anti-TNFα therapy induces a distinct regulatory T cell population in patients with rheumatoid arthritis via TGF-β, JEM Vol. 204, p. 33-39.

Bresson et al. (2006) suggest the treatment of type I diabetes by combined administration of an anti-CD3ε specific antibody and a proinsulin peptide.

Vandenbark et al. (2008), Therapeutic vaccination with a trivalent T-cell receptor (TCR) peptide vaccine restores deficient FoxP3 expression and TCR recognition in subjects with multiple sclerosis, Immunology Vol. 123, p. 66-78, describe an improvement in the control of the autoreactive response in multiple sclerosis after vaccination of the patients with certain TCR peptides.

Although these newer substances act very specifically, severe side-effects can occur, e.g., the onset of progressive multifocal leukoencephalopathy. For this reason, only three months after its first registration in the USA, natalizumab was again withdrawn from the market. The costs of these new active substances are very high. At present, 300 mg of natalizumab costs over 2,000.00 Euros. 200 mg of infliximab costs, ca. 1,700.00 Euros.

SUMMARY OF THE INVENTION

Against this background, the purpose of the present invention is to provide a new pharmaceutical composition for the treatment and/or prophylaxis of an autoimmune disease, with which the disadvantages due to the state of the art are as far as possible avoided. In particular, a pharmaceutical composition which is characterized by good tolerance and low toxicity should be provided.

A further purpose of the present invention is to provide an agent for the formation of regulatory T cells ($T_{Reg}$) in an organism.

These problems are solved through the provision of a mutein of human interleukin 2 (hIL-2 mutein) or a section or fragment thereof, which is numbered in accordance with the hIL-2 wild type and has an amino acid substitution in at least one of the positions 20, 88 or 126.

The inventors have surprisingly discovered that such an hIL-2 mutein or a fragment thereof has high therapeutic potential which can be utilized for the treatment and prophylaxis of autoimmune diseases. Thus for example they were able to demonstrate in various experimental preparations that the hIL-2 mutein selectively induces the formation of regulatory T cells such as $CD4^+CD25^+Foxp3^+$ and $CD4^+CD25^-Foxp3^+$ in an organism.

Surprisingly, the hIL-2 mutein according to the invention displays markedly higher activity on the regulatory T cells than hIL-2 wild type. This is particularly apparent at high concentrations.

For the hIL-2 mutein, according to the invention it is disclosed in WO 99/60128 that it binds more strongly to the triple-chain IL-2 receptor (IL-2Rαβγ) than to the double-chain IL-2 receptor (IL-2Rβγ). As the inventors have now been able to show for the first time, compared to hIL-2 wild type, the hIL-2 mutein according to the invention induces, but surprisingly also intensifies, the formation of those regulatory T cells which lack the a subunit of the IL-2 receptor (CD25) ($CD4^+CD25^-Foxp3^+$). This subpopulation in addition contributes to the suppression of the activation of the immune system and thereby to the regulation of the self-tolerance of the immune system. As a result, the hIL-2 mutein according to the invention displays considerably higher potency as an active substance for the treatment of autoimmune diseases than the hIL-2 wild type.

The inventors were also able to demonstrate that a hIL-2 mutein induces the formation of CD8 positive regulatory T cells, such as $CD3^+CD4^-CD25^+Foxp3^+$ and $CD3^+CD4^-CD25^-Foxp3^+$ (data not shown) which play a decisive role in the suppression of autoimmune diseases.

In addition, the hIL-2 mutein according to the invention has the further advantage compared to hIL-2 wild type that it selectively activates T cells as opposed to natural killer cells (NK cells) and as a result displays a reduced toxicity profile and an increased therapeutic index. As a result, the hIL-2 mutein according to the invention is considerably better tolerated than the hIL-2 wild type; see WO 99/60128.

Further, on the basis of the cytotoxic $CD3^+CD8^+$ $CD45RO^+$ T cells it could for the first time be shown that in contrast to the hIL-2 wild type the hIL-2 mutein according to the invention surprisingly has no or only a slight effect on the proliferation of CD8-positive cytotoxic T cells which are also described as "naïve, central memory, early differentiated" and "late differentiated" CD8 T cells. This is advantageous insofar as the $CD8^+$-cytotoxic T cells are held to be responsible for persistent, chronic inflammatory processes in autoimmune diseases; cf. Liu et al. (2007), Multiple Sclerosis, 13, p. 149, and Haegele et al. (2007), Neuroimmunol, 183, p. 168). Thus, compared to the hIL-2 wild type, the hIL-2 mutein according to the invention prevents a further intensification of this inflammatory reaction caused by the $CD8^+$ T cells, which represents a further tolerance advantage.

As the inventors were also able to show, the hIL-2 mutein according to the invention also stimulates the antigen-specific activity of the immune cells. This has the advantage that, by means of the hIL-2 mutein, disease-specific immune cells are selectively stimulated and thereby the systemic effect of the immune therapy is limited. As a result, induction of other diseases due to the administration of the hIL-2 mutein is also prevented.

Further, on the basis of a murine model of type I diabetes mellitus, the inventors were able to show that the onset of an autoimmune disease can be prevented by the treatment with the hIL-2 mutein according to the invention.

The problem underlying the invention is thus completely solved.

According to the invention, "wild type" of human interleukin 2 (hIL-2 wild type) is understood to mean a polypeptide or protein which has the amino acid sequence of 133 amino acids which is present in natural human IL-2 (without the signal peptide which consists of a further 20 N-terminal amino acids) hIL-2 wild type can be expressed both naturally and also recombinantly. The amino acid sequence of hIL-2 wild type is described in Fujita et al. (1983), PNAS USA 80, p. 7437-7441, both with and without an additional N-terminal methionine, which is necessarily present when the protein is expressed in E. coli as an intracellular fraction. The amino acid sequence of the hIL-2 wild type is disclosed in the attached sequence protocol under SEQ ID NO:1. The nucleotide sequence of the cDNA which encodes for hIL-2 is disclosed in the attached sequence protocol under SEQ ID NO:2.

According to the invention, a "mutein" of human interleukin 2 (hIL-2 mutein) is understood to mean a polypeptide or protein in which compared to hIL-2 wild type specific substitutions have been effected. The identification of the positions at which substitutions have been effected is based on the positions of the amino acids in the hIL-2 wild type, which can for example be taken from SEQ ID NO:1. Accordingly, an alanine (A) is located at position 1, a proline (P) at position 2, a threonine (T) at position 133, etc. The aspartic acid residue (D) at position 20 ("D20") can for example be replaced by an isoleucine residue (I) or a histidine (H), so that IL-2 muteins which are described as hIL-2-D20I and hIL-2-D20H, respectively, are formed.

It goes without saying that the hIL-2 mutein according to the invention can be substituted at several of the stated positions 20, 88 or 126, so that combination mutants which are particularly suitable for the treatment of an autoimmune disease or for the induction of regulatory T cells are formed.

According to the invention, an hIL-2 mutein also includes a modified polypeptide, for example a glycosylated hIL-2 mutein. Glycosylated hIL-2 muteins are for example disclosed in the U.S. patent application Ser. Nos. 09/310,026 and 10/051,657, which are incorporated herein by reference.

According to the invention, a "section" or "fragment" of hIL-2 mutein is understood to mean a polypeptide in which compared to the hIL-2 mutein one or more amino acids are missing at the N- and/or C-terminus, but this nonetheless still exhibits sufficient biological activity of the hIL-2 mutein to be used according to the invention for the treatment and/or prophylaxis of autoimmune diseases. This activity is regarded as sufficient if the section or fragment exhibits at least 50%, preferably at least 60%, more preferably at least 70%, more preferably at least 80%, more preferably at least 90% and most preferably at least 95% of the activity of the hIL-2 mutein for the induction of regulatory T cells. The activity of the hIL-2 mutein can easily be measured by methods known to the person skilled in the art. Such a method is for example disclosed in WO 99/60128, examples 3 to 5. By reference, this publication is incorporated into the present disclosure.

According to the invention it is preferable if the substitutions at the stated positions are not conservative substitutions whereby one amino acid is exchanged for another with similar biochemical properties.

In this respect, it is preferable if the substitution at position 20 is not one in which the aspartic acid (D) is exchanged for a glutamic acid (E). Preferably the substitution at position 88 is not one in which the asparagine (N) is exchanged for an alanine (A), proline (P), glycine (G), glutamine (Q), serine (S) or threonine (T). Further, the substitution at position 126 is preferably not one in which the glutamine (Q) is exchanged for an alanine (A), proline (P), glycine (G), asparagine (N), serine (S) or threonine (T). These substitutions would not or only insignificantly alter the biological activity of the hIL-2 wild type.

Further, it is preferable if no substitutions which introduce sites for intermolecular cross-linking or incorrect disulphide bridge linkages are effected at the stated positions. Hence the substitution of the hIL-2 mutein according to the invention at position 20 is preferably not one in which the aspartic acid (D) is exchanged for arginine (R), asparagine (N), aspartic acid (D), cysteine (C), glutamic acid (E), glycine (G), leucine (L), lysine (K), phenylalanine (F), proline (P), threonine (T) or tryptophan (W). The substitution at position 88 is preferably not one in which the asparagine (N) is exchanged for aspartic acid (D), cysteine (C), glutamine (Q), tryptophan (W) or proline (P). The substitution at position 126 is preferably not one in which the glutamine (Q) is exchanged for an alanine (A), histidine (H), tryptophan (W), cysteine (C), glutamine (Q), glutamic acid (E) or lysine (K).

The hIL-2 mutein according to the invention can be prepared by any suitable method known in the state of the art. Such methods comprise the construction of a DNA sequence which encodes for the IL mutein according to the invention and for example includes the nucleotide sequence SEQ ID NO:2 and the expression of this sequence in a suitable host. This method leads to the muteins according to the invention in recombinant form. However, the mutein according to the invention can also be prepared by chemical synthesis or a combination of chemical synthesis and recombinant DNA technology. The preparation of the mutein according to the invention is described in detail in WO 99/60128, embodiments 1 and 2, which are incorporated by reference into the present disclosure.

A particularly preferred hIL-2 mutein according to the invention, in which at position 88 the asparagine (N) is exchanged for an arginine (R) (hIL-2-N88R), is available to the person skilled in the art under the name BAY50-4798; see Shanafelt et al. (2000), A T-cell-selective interleukin 2 mutein exhibits potent antitumor activity and is well tolerated in vivo, Nat. Biotechnol. Vol. 18, p. 1197-1202. The amino acid sequence of hIL-2-N88R is disclosed in the appended sequence protocol under SEQ ID NO:3.

The inventors' discoveries were especially surprising in that in the state of the art no indications whatever of such activity of the IL-2 mutein are to be found.

Thus in WO 99/60128 for the mutein hIL-2-N88R it is disclosed that this can selectively activate T cells as opposed to natural killer cells and is capable of reducing metastasis formation in the lung.

In WO 02/00243, a stable, histidine-containing, albumin-free formulation for the mutein hIL-2-N88R is described.

In US 2002/0164300, a glycosylated variant of the mutein hIL-2-N88R is described.

The use of the hIL-2 mutein according to the invention for the targeted treatment and/or prophylaxis of autoimmune diseases or for the selective activation of regulatory T cells in an organism, is neither described nor rendered obvious in the state of the art.

Even for the human wild type IL-2, there are no corresponding discoveries.

Van der Vliet et al. (2007), Effects of the administration of high-dose interleukin-2 on immunoregulatory cell subsets in patients with advanced melanoma and renal cell cancer, Clin. Cancer Res. Vol. 13, p. 2100-2108, report that on administration of high doses of IL-2 its therapeutic efficacy for the treatment of tumours is reduced.

Ahmadzadeh and Rosenberg (2006), IL-2 administration increases $CD4^+CD25^{hi}Foxp3^+$ regulatory T cells in cancer patients, Blood, Vol. 107, p. 2409-2414, propose improving the therapeutic efficacy of human wild type IL-2 in tumour patients by eliminating the patients' regulatory T cells. However, this approach turned out not to be promising; see Powell et al. (2007), Inability to mediate prolonged reduction of regulatory T cells after transfer of autologous CD25-depleted PBMC and interleukin-2 after lymphodepleting chemotherapy, J. Immunother. Vol. 30, p. 438-447.

Antony and Restifo (2005), CD4+CD25+ T regulatory cells, immunotherapy of cancer, and interleukin-2, J. Immunother. Vol. 28, p. 120-128, rather discount IL-2 as an immuno-therapeutic agent and even report that the administration of IL-2 can induce autoimmunity.

Knoechel et al. (2005), Sequential development of interleukin 2-dependent effector and regulatory T cells in response to endogenous systemic antigen, JEM Vol. 202, p. 1375-1386, incline to the same view and even suggest IL-2 antagonism, i.e., inhibition of IL-2 mechanisms, in order to treat the early phase of autoimmune diseases.

Hence in the state of the art there are no clues that render the solution according to the invention obvious.

Thus the inventors have also discovered that the therapeutic effects of hIL-2 mutein can be different depending on the indication and the concentration used. A high concentration of hIL-2 can be advantageous for the treatment of autoimmune diseases, but be contra-indicated in the therapy of tumour diseases.

In the use according to the invention it is preferable if through the substitution at position 88 an asparagine is exchanged for an arginine (hIL-2-N88R), or for a glycine (hIL-2-N88G), or for an isoleucine (hIL-2-N88I), and/or through the substitution at position 20 an aspartic acid is exchanged for a histidine (hIL-2-D20H), or for an isoleucine (hIL-2-D20I), or for a tyrosine (hIL-2-D20Y), or through the substitution at position 126 a glutamine is exchanged for a leucine (hIL-2-Q126L).

This measure has the advantage that an hIL-2 mutein according to the invention which is distinguished in that it particularly selectively activates T cells as opposed to natural killer cells and hence exhibits a high therapeutic potential and low toxicity is used. These properties of the preferred hIL-2 muteins according to the invention are described in WO 99/60128, which is incorporated by reference into the present disclosure.

According to the invention it is preferable if the hIL-2 mutein or the fragment thereof has at least one further amino acid substitution in any position except the positions 20, 88 or 126 so that the thus further substituted hIL-2 mutein or the thus further substituted section or fragment thereof has an amino acid sequence which is at least 80%, preferably 85%, more preferably 90%, more preferably 95%, most preferably 99% identical with the amino acid sequence of the hIL-2 mutein or of the section or fragment thereof, which is not further substituted compared to the hIL-2 wild type, apart from in at least one of the positions 20, 88 or 126.

This measure has the advantage that alternative primary structures are provided, which are in some cases easier to synthesize than the hIL-2 mutein, which apart from in at least one of the positions 20, 88 or 126 otherwise corresponds to the hIL-2 wild type. In order to obtain a polypeptide with the biological activity of the hIL-2 mutein or of the section thereof and hence a drug for the treatment and/or prophylaxis of an autoimmune disease, it is not absolutely necessary to provide a polypeptide which has an amino acid sequence which is 100% identical with the amino acid sequence of the hIL-2 mutein or section thereof according to the invention. Rather, it is sufficient if adequately high identity is present, while if necessary moderate activity losses are tolerable, but preferably at least 50%, 60%, 70%, 80%, 90%, 95% or 99% of the activity is retained. The stated identities are based on a section of the hIL-2 mutein according to the invention with ≥10 amino acids. The degree of homology can easily be determined by methods known to the person skilled in the art, for example a BLAST analysis, or using the MegAlign module of the Lasergene program from DNAStar Inc.

According to the invention it is further preferred if the further amino acid substitution in any position except the positions 20, 88 or 126 is a conservative amino acid substitution.

This measure has the advantage that further variants of the hIL-2 mutein according to the invention that exhibit sufficiently high activity for the treatment and/or prophylaxis of autoimmune diseases or for the induction of regulatory T cells in an organism are provided. It is known to the person skilled in the art that conservative substitutions have no or only a minimal effect on the secondary or tertiary structure of the mutein. Such conservative substitutions include those which are described by Dayhoff in "The Atlas of Protein Sequence and Structure. Vol. 5", Natl. Biomedical Research. For example, amino acids which belong to one of the following groups can be exchanged for one another, i.e., constitute a conservative exchange:

Alanine (A), proline (P), glycine (G), asparagine (N), serine (S), threonine (T);
Cysteine (C), serine (S), tyrosine (Y), threonine (T);
Valine (V), isoleucine (I), leucine (L), methionine (M), alanine (A), phenylalanine (F);
Lysine (K), arginine (R), histidine (H);
Phenylalanine (F), tyrosine (Y), tryptophan (W), histidine (H); and
Aspartic acid (D), glutamic acid (E).

The agent according to the invention for the induction of the formation of regulatory T cells in an organism is preferably a pharmaceutical composition which contains a pharmaceutically acceptable carrier.

This measure has the advantage that the agent is already provided in a form which enables direct administration to the organism, preferably to a person.

Pharmaceutically acceptable carriers are comprehensively described in the state of the art; see Row et al. (2006), Handbook of Pharmaceutical Excipients, 5$^{th}$ Edition, Pharmaceutical Press and American Pharmacists' Association; Bauer et al. (1999), Lehrbuch der pharmazeutischen Technologie, Wissenschaftliche Verlagsgesellschaft mbH Stuttgart. A particularly preferred formulation is that which is disclosed in WO 02/00243, which by reference is a component of the present disclosure. This formulation is albumin-free and the stabilization of the hIL-2 mutein or section thereof is effected with histidine. Preferably the finished drug has the following components in the following concentrations: hIL-2 mutein or a section thereof=0.1-5 mg/ml; histidine=0.08-1.6 wt. %; NaCl=0-0.9 wt. %; saccharose=1-10 wt. %; glycine=0-0.3 wt. %, and has a pH value of ca. 5 to 6.5.

According to a particular embodiment, the pharmaceutical composition also contains an immunosuppressant.

On account of the especial potency of the hIL-2 mutein according to the invention, the pharmaceutical composition can already be used as a monopreparation for the treatment and/or prophylaxis of autoimmune diseases. Such a monopreparation contains the hIL-2 mutein according to the invention as the only active substance. In this context, pharmaceutically acceptable carriers, solvents (buffers, water, etc.), additives, etc., are not active substances.

This measure has the advantage that the therapeutic index of the drug according to the invention is further increased by inclusion of a standard immunosuppressant.

Preferably the immunosuppressant is selected from the group consisting of glucocorticoid, including decortin, prednisol; azathioprine; cyclosporin A; mycophenolate mofetil; tacrolimus; anti-T lymphocyte globulin, anti-CD3 antibodies, including muromonab; anti-CD25 antibodies, including basiliximab and daclizumab; anti-TNF-α antibodies, including infliximab and adalimumab; azathioprine; methotrexate; cyclosporin; sirolimus; everolimus; fingolimod; CellCept®; myfortic and cyclophosphamide.

This measure has the advantage that an immunosuppressant which has demonstrably therapeutic activity in autoimmune diseases and is sufficiently available in the state of the art is used.

Further, it is preferable if the autoimmune disease is selected from the group consisting of: type I diabetes mellitus, rheumatoid arthritis, multiple sclerosis, chronic gastritis, Crohn's disease, Basedow disease, Bechterew disease, psoriasis, myasthenia gravis, autoimmune hepatitis, APECED, Chrug-Strauss syndrome, ulcerative colitis, glomerulonephritis, Guillain-Barré syndrome, Hashimoto thyroiditis, lichen sclerosus, systemic lupus erythematodes, PANDAS, rheumatic fever, sarcoidosis, Sjörgren syndrome, Stiff-Man syndrome, scleroderma, Wegener's granulomatosis, vitiligo, autoimmune enteropathy, Goodpasture syndrome, dermatomyositis, polymyositis, autoimmune allergy, asthma and autoimmune reaction after organ transplantations.

This measure has the advantage that a drug which can be used for the treatment and/or prophylaxis of the most important autoimmune diseases is provided.

A further subject of the present invention relates to a pharmaceutical composition for the treatment and/or prophylaxis of an autoimmune disease, which contains the hIL-2 mutein according to the invention or a fragment thereof.

The properties and advantages and definitions described in connection with the use according to the invention likewise apply for the pharmaceutical composition according to the invention.

A further subject of the present invention relates to an agent for the formation of regulatory T cells ($T_{Reg}$) in an organism, which contains the hIL-2 mutein according to the invention or a fragment thereof.

The advantages and properties and definitions of the use according to the invention likewise apply for the agent according to the invention.

Further subjects of the present invention are methods for the treatment and/or prophylaxis of an autoimmune disease in an organism and for the formation of regulatory T cells ($T_{Reg}$) in an organism, which each comprise the following steps: (a) provision of a mutein of human interleukin 2 (hIL-2 mutein) or of a fragment thereof, (b) administration of the hIL-2 mutein or of the section thereof to an organism, and (c) if necessary repetition of the steps (a) and (b), where the hIL-2 mutein or the section thereof is the hIL-2 mutein according to the invention or a section thereof.

The organism is preferably a mammal, more preferably a human organism.

The properties and advantages and definitions described in connection with the use according to the invention likewise apply for the aforesaid methods according to the invention for the treatment and/or prophylaxis of an autoimmune disease in an organism and for the formation of regulatory T cells ($T_{Reg}$) in an organism.

A further subject of the present invention relates to a method for the formation of regulatory T cells ($T_{Reg}$) in vitro, which comprises the following steps: (a) provision of a mutein of human interleukin-2 (hIL-2 mutein) or of a fragment thereof, (b) contacting of the hIL-2 mutein or of the fragment thereof with peripheral mononuclear blood cells (PBMCs), and (c) if necessary repetition of the steps (a) and (b), where the hIL-2 mutein or the fragment thereof is the hIL-2 mutein according to the invention or a fragment thereof.

The contacting of hIL-2 or of the fragments thereof with the PBMCs can be effected in any suitable medium for the culturing of the PBMCs.

The properties and advantages and definitions described in connection with the use according to the invention likewise apply for the aforesaid method according to the invention for the formation of regulatory T cells ($T_{Reg}$) in vitro.

A further subject of the present invention relates to a method for the treatment and/or prophylaxis of an autoimmune disease in an organism, which comprises the following steps: (a) provision of a mutein of human interleukin-2 (hIL-2 mutein) or of a fragment thereof, (b) contacting of the hIL-2 mutein or of the fragment thereof with peripheral mononuclear blood cells (PBMCs) deriving from a first organism, (c) incubation of the hIL-2 mutein or of the fragment thereof with the PBMCs, in order to obtain a cell population which contains regulatory T cells ($T_{Reg}$), and (d) introduction of the cell population into a second organism, where the hIL-2 mutein or the fragment thereof is the hIL-2 mutein according to the invention or a fragment thereof.

The first organism and the second organism preferably have the identical blood group, it being particularly preferred if the first and the second organisms are identical organisms or individuals.

Here it is advantageous that in the introduction or reinfusion of the cell population no undesired immune reactions against the cells occur and the method is therefore particularly low in side-effects.

The properties and advantages and definitions described in connection with the use according to the invention likewise apply for the aforesaid method according to the invention for the treatment and/or prophylaxis of an autoimmune disease in an organism.

It goes without saying that the features stated above and those still to be explained below are usable not only in the particular combination stated, but also in other combinations or alone, without departing from the scope of the present invention.

Below, the invention is explained in more detail on the basis of practical examples, which are purely of an exemplary nature and do not restrict the scope of the invention. In these, reference is made to the appended figures.

EMBODIMENTS

Figure 1:
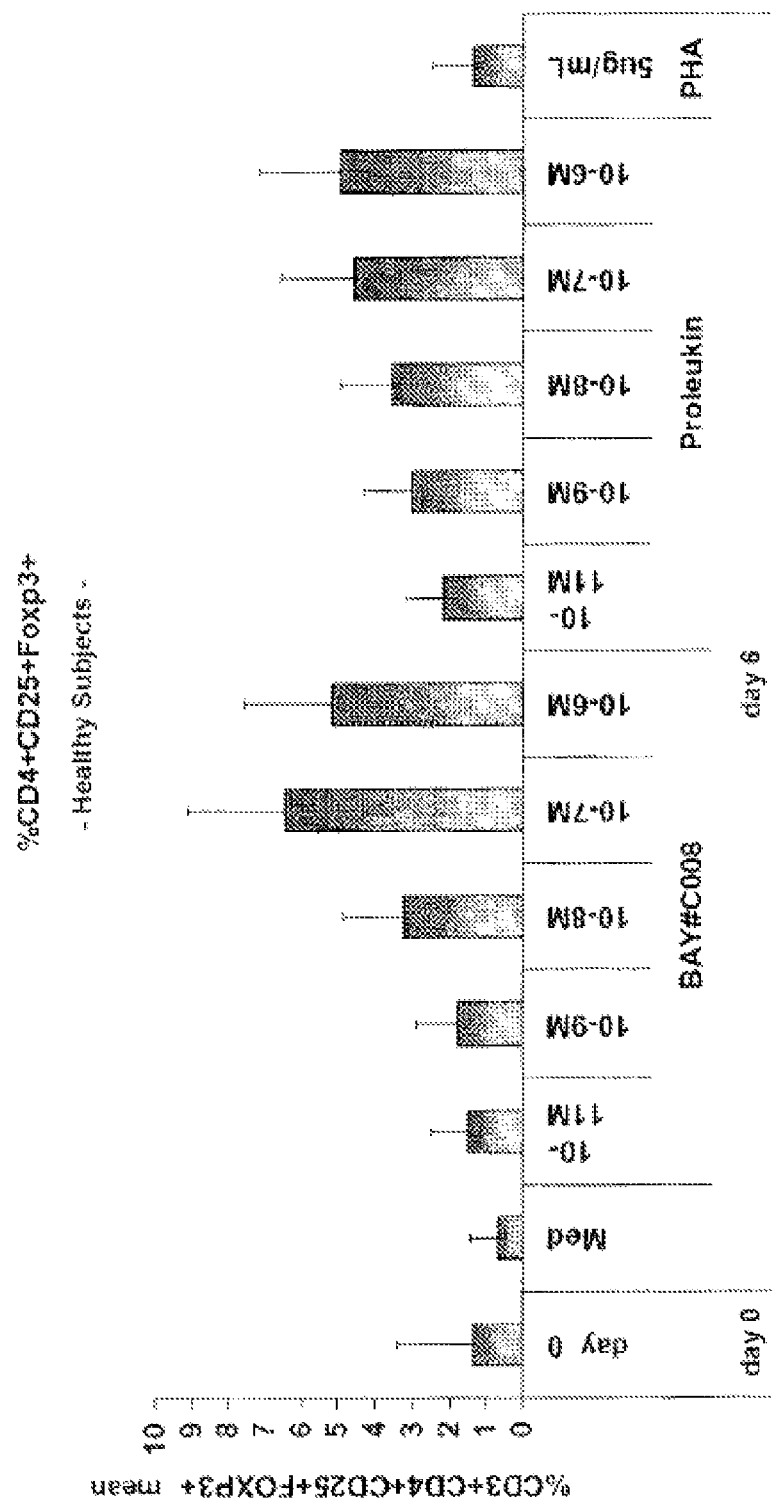
FIG. 1 shows that hIL-2-N88R in healthy subjects at equal or lower dosage in comparison to proleukin induces a greater increase in the regulatory $CD4^+CD25^+Foxp3^+$ T cells.

1. Material and Methods 1.1 Separation of PBMCs from Whole Blood for Use In Vitro Peripheral mononuclear blood cells (PBMCs) from healthy subjects, melanoma patients or MS patients are separated from the blood by means of lymphocyte separation medium (Histopaque, Sigma Aldrich). For this, two tubes of blood (7 or 10 ml) from the same subject or patient are transferred into a sterile 50 ml tube and made up to 30 ml with RPMI 1640 (InVitrogen, #14190-69). Next, 30 ml of the diluted blood are layered onto 15 ml of a density gradient solution (density=1.077; Histopaque, Sigma Aldrich, #10771).

After centrifugation at 400 g for 40 min at 20° C. without braking, two "white blood cell rings" are harvested and transferred into a sterile 50 ml tube and washed twice with phosphate buffered saline (PBS; InVitrogen #14190-169). In the event of contamination with red blood cells, an RBC ("red blood cells") lysis is performed; 2 ml of RBC lysis solution are added to the cell pellet and incubation is performed for 2 min with gentle mixing at room temperature, followed by a washing procedure with a large volume of complete medium (RPMI 1640 with 10% fetal calf serum).

The number of live leucocytes is determined by exclusion staining using trypan blue (InVitrogen #15250-061) and a haemocytometer (FisherBioblock A2759B).

1.2 CFSE Labelling

After counting, the cells are washed twice in PBS and resuspended in PBS at a concentration of 1×10$^6$ cells/ml. CFSE (InVitrogen # C1157) is added at a final concentration of 0.5 µM. After 10-minute incubation in the dark at 37° C., the CFSE-labelled cells are washed three times with fresh complete medium at 4° C. and resuspended in complete medium at a concentration of 1×10$^6$ cells/ml for plating out.

1.3 Stimulation of the PBMCs In Vitro

The PBMCs either remain unstimulated or are stimulated with hIL-2 wild type (proleukin) or hIL-2-N88R (BAY 50-4798; Lot #PR312C008) with or without a pool of synthetic peptides, which are derived from the melanoma-specific proteins gp100, TRP-2, MART-1 and tyrosinase or from the protein MOG specific for multiple sclerosis (MS), each peptide being added in a final concentration of 2.5 µM (melanoma peptide) or 30 µg/ml (MS peptide).

Stimulator and peptide are added under the following 23 conditions:

TABLE 1

Conditions for stimulation of PBMCs

| Condition | Stimulator | Final concentration | |
|---|---|---|---|
| 1 | hIL-2-N88R (BAY 50-4798; #PR312C008) | 10$^{-11}$M | no peptides |
| 2 | hIL-2-N88R (BAY 50-4798; #PR312C008) | 10$^{-11}$M | peptides |
| 3 | hIL-2-N88R (BAY 50-4798; #PR312C008) | 10$^{-9}$M | no peptides |
| 4 | hIL-2-N88R (BAY 50-4798; #PR312C008) | 10$^{-9}$M | peptides |
| 5 | hIL-2-N88R (BAY 50-4798; #PR312C008) | 10$^{-8}$M | no peptides |
| 6 | hIL-2-N88R (BAY 50-4798; #PR312C008) | 10$^{-8}$M | peptides |
| 7 | hIL-2-N88R (BAY 50-4798; #PR312C008) | 10$^{-7}$M | no peptides |
| 8 | hIL-2-N88R (BAY 50-4798; #PR312C008) | 10$^{-7}$M | peptides |
| 9 | hIL-2-N88R (BAY 50-4798; #PR312C008) | 10$^{-6}$M | no peptides |
| 10 | hIL-2-N88R (BAY 50-4798; #PR312C008) | 10$^{-6}$M | peptides |
| 11 | hIL-2 wild type (proleukin) | 10$^{-11}$M | no peptides |
| 12 | hIL-2 wild type (proleukin) | 10$^{-11}$M | peptides |
| 13 | hIL-2 wild type (proleukin) | 10$^{-9}$M | no peptides |
| 14 | hIL-2 wild type (proleukin) | 10$^{-9}$M | peptides |
| 15 | hIL-2 wild type (proleukin) | 10$^{-8}$M | no peptides |
| 16 | hIL-2 wild type (proleukin) | 10$^{-8}$M | peptides |
| 17 | hIL-2 wild type (proleukin) | 10$^{-7}$M | no peptides |
| 18 | hIL-2 wild type (proleukin) | 10$^{-7}$M | peptides |
| 19 | hIL-2 wild type (proleukin) | 10$^{-6}$M | no peptides |
| 20 | hIL-2 wild type (proleukin) | 10$^{-6}$M | peptides |
| 21 | PHA | 5 µg/ml | |
| 22 | unstim. | | |
| 23 | peptide only | | peptides |

Next the cells were cultured for six days at 37° C. in an atmosphere with 5% CO$_2$ content.

1.4 Proliferation Assay and Phenotyping on the FC500 Flow Cytometer

The staining of the cells with fluorescence-labelled antibodies to cell surface molecules makes it possible to study the proliferation of a specific subgroup of lymphocytes (memory and activation markers, see Tab. 2). The immunostaining with fluorochrome-labelled (PE: phycoerythrin, ECD: PE-Texas Red, APC: allophycocyanin, PC7: PE-Cy7) antibodies is performed before and after six days of culturing with the stimulators.

On the sixth day, the first two stainings (1 and 1iso) are performed with non-CFSE-labelled cells (CFSE: carboxyfluorescein diacetate succinimidyl ester); the other stainings are performed on CFSE-labelled cells.

TABLE 2

Staining scheme for PBMCS

|   | PE | ECD | APC | PC7 |
|---|---|---|---|---|
| 1 | CD25 | CD45 | Foxp3 | CD4 |
| 1iso | CD25 | CD45 | Rat IgG2a | CD4 |
| 2 | CD127 | CD45 | CD25 | CD4 |
| 3 | CD3 | CD45 | CD25 | CD8 |
| 4 | CD16 |  | CD56 | CD3 |
| 5 | CCR7 | CD3 | CD45RA | CD4 |
| 6 | CCR7 | CD3 | CD45RA | CD8 |
| 7 | CD8 | CD3 | CD45RO | CD4 |
| 1 | CD25 | CD3 | Foxp3 | CD4 |
| 1iso | CD25 | CD3 | Rat IgG2a | CD4 |
| 2 | CD8 | CD3 | CD25 | CD4 |
| 3 | CCR7 | CD3 | CD45RA | CD4 |
| 4 | CD8 | CD3 | CD45RO | CD4 |

CD25-PE, Foxp3-APC and rat IgG2a-APC are from ebiosciences; CD25-APC, CD45RA-APC and CD45RO-APC were purchased from BD Biosciences. All other antibodies are from Beckman-Coulter, France.

1.5 Type I Mouse Diabetes Model 12 week old NOD ("non-obese diabetes") mice are treated daily with hIL-2 mutein or hIL-2 wild type. Negative control animals were analogously treated with physiological salt solution (saline). The treatment groups consisted of 3-5 animals. On day 0 to 15, a quantity of 5K or 25K-units of hIL-2 mutein or hIL-2 wild type was administered to the mice. From day 17, in the treatment groups with 5K units, this was increased to 100K-units (=6.112 µg). The treatment of the animals with 25K-units was maintained unchanged. The last dosing was performed on day 31. In a parallel experiment, treatment was performed from day 0 to day 31 with a fixed dose of 25K-units. Diabetes was detected by monitoring of glucose levels in the urine. Blood samples were taken from the mice on day 17 and day 30. The samples were analyzed in the FACS using anti-CD4, anti-CD25 and anti-FoxP3 staining and the percentage of FoxP3$^+$ cells among the CD4$^+$ T cells and the mean fluorescence intensity (MFI) of the CD25 expression on CD4$^+$FoxP3$^+$ cells was thus determined.

2. Results 2.1 Induction of Regulatory T Cells by hIL-2-N88R

As a suitable in-vitro system for testing the effect of the muteins according to the invention, peripheral mononuclear blood cells (PBMCs) were used. PBMCs consist of T cells (~75% CD4- and CD8-positive) and B and NK cells (~25% positive) and thus constitute a cell population well representing the immune system.

PBMCs from six healthy subjects (10$^6$ cells/ml) were stimulated with wild type IL-2 (proleukin) or IL-2-N88R [BAY 50-4798, Lot #PR312C008 ("BAY#C008")] at concentrations which lay between 10$^{-11}$ and 10$^{-6}$ M, or in the positive control with the non-specific mitogen phytohaemagglutinin ("PHA") at a concentration of 5 µg/ml or with culture medium only ("Med"). On day 0 and on the sixth day after the stimulation, the content of the regulatory CD4$^+$CD25$^+$Foxp3$^+$ T cells within the CD3$^+$ lymphocytes was determined. The result is shown in FIG. 1 and the following Table 3.

TABLE 3

Percentage of CD3$^+$CD4$^+$CD25$^+$Foxp3$^+$ T cells after stimulation; mean values from six healthy subjects; S.D.: standard deviation

| Conditions |  | Mean value | S.D. |
|---|---|---|---|
| day 0 | day 0 | 1.367 | 2.060 |
|  | Med | 0.683 | 0.741 |
| hIL-2-N88R (BAY#C008) ##1C008) | 10$^{-11}$M | 1.483 | 1.017 |
|  | 10$^{-9}$M | 1.783 | 1.153 |
|  | 10$^{-8}$M | 3.267 | 1.596 |
|  | 10$^{-7}$M | 6.483 | 2.642 |
|  | 10$^{-6}$M | 5.200 | 2.375 |
| hIL-2 wild type (proleukin) | 10$^{-11}$M | 2.183 | 1.030 |
|  | 10$^{-9}$M | 3.067 | 1.255 |
|  | 10$^{-8}$M | 3.600 | 1.330 |
|  | 10$^{-7}$M | 4.600 | 1.992 |
|  | 10$^{-6}$M | 4.967 | 2.199 |
| PHA | 5 µg/ml | 1.400 | 1.081 |
| peptide only |  | 1.340 | 0.680 |

From this experiment it follows that hIL-2-N88R at concentrations of 10$^{-7}$ M and 10$^{-6}$ M leads to marked induction of the subpopulation of the regulatory T cells CD4$^+$CD25$^+$Foxp3$^+$. The induction here is markedly greater than with stimulation of the PBMCs by hIL-2 wild type.

Figure 2:
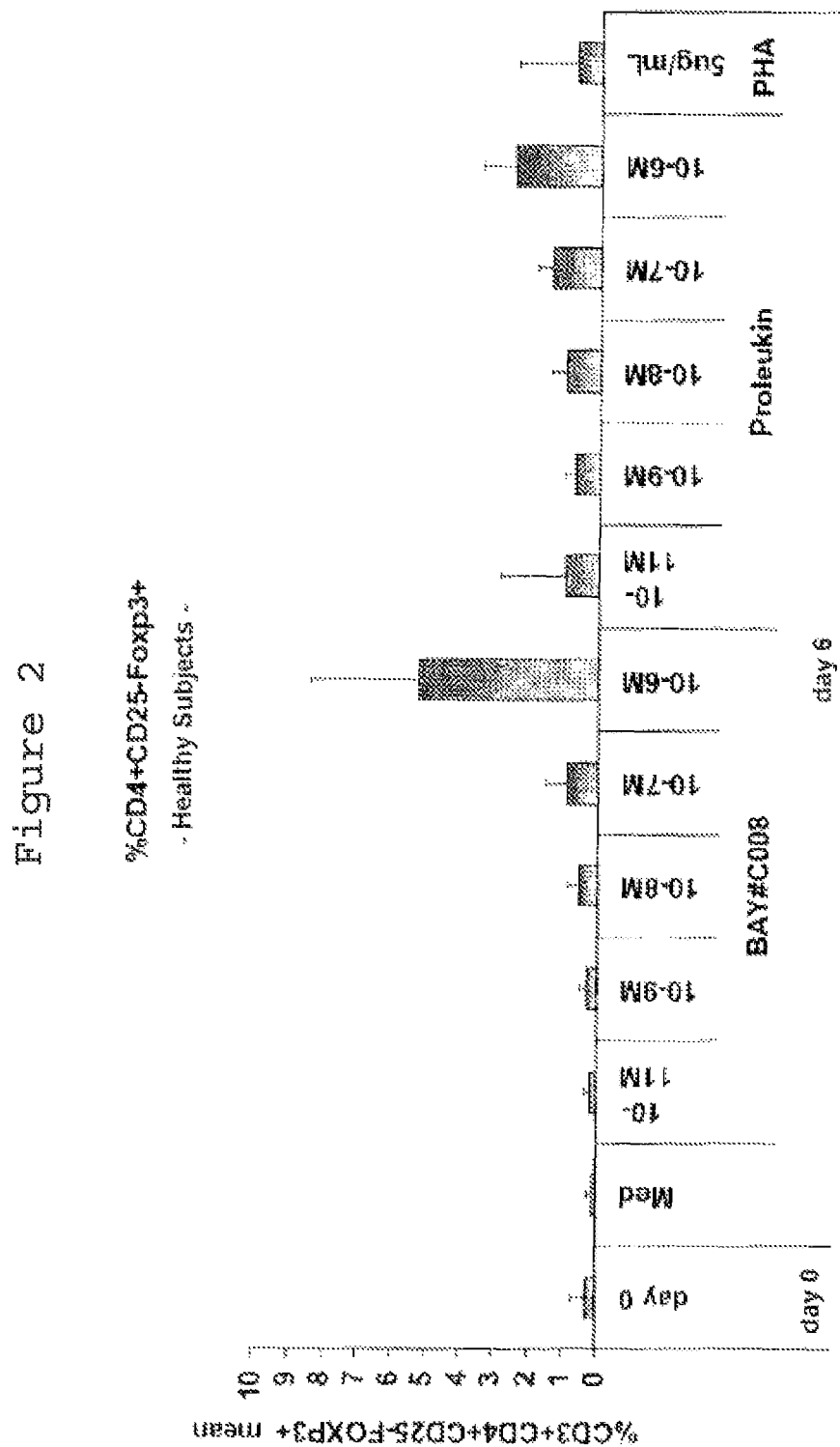
FIG. 2 shows that hIL-2-N88R in healthy subjects at equal or lower dosage in comparison to proleukin induces a greater increase in the regulatory $CD4^+CD25^-Foxp3^+$ T cells.

In a second preparation, the increase in the subpopulation of the regulatory T cells CD4$^+$CD25$^-$Foxp3$^+$ after stimulation with hIL-2-N88R in comparison to hIL-2 wild type was studied. The result is shown in FIG. 2 and the following Table 4.

TABLE 4

Percentage of CD3$^+$CD4$^+$CD25$^-$Foxp3$^+$ T cells after stimulation; mean values from six healthy subjects

| Conditions |  | Mean Value | S.D. |
|---|---|---|---|
| day 0 | day 0 | 0.317 | 0.402 |
| day 6 | Med | 0.133 | 0.151 |
| hIL-2-N88R (BAY#C008) #1C008) | 10$^{-11}$M | 0.200 | 0.141 |
|  | 10$^{-9}$M | 0.320 | 0.179 |
|  | 10$^{-8}$M | 0.517 | 0.354 |
|  | 10$^{-7}$M | 0.917 | 0.601 |
|  | 10$^{-6}$M | 5.250 | 3.141 |
| hIL-2 wild type (proleukin) | 10$^{-11}$M | 1.000 | 1.864 |
|  | 10$^{-9}$M | 0.717 | 0.293 |
|  | 10$^{-8}$M | 1.000 | 0.429 |
|  | 10$^{-7}$M | 1.433 | 0.403 |
|  | 10$^{-6}$M | 2.533 | 0.903 |
| PHA | 5 µg/ml | 0.700 | 1.715 |
| peptide only |  | 0.160 | 0.089 |

Here too, it is seen that the stimulation with hIL-2-N88R leads to a marked increase in the subpopulation of the regulatory T cells CD4$^+$CD25$^-$Foxp3$^+$, which at concentrations of 10$^{-6}$ M is markedly greater than with stimulation with hIL-2 wild type.

2.2 hIL-2-N88R Induces Regulatory T Cells in Melanoma Patients

Figure 3:
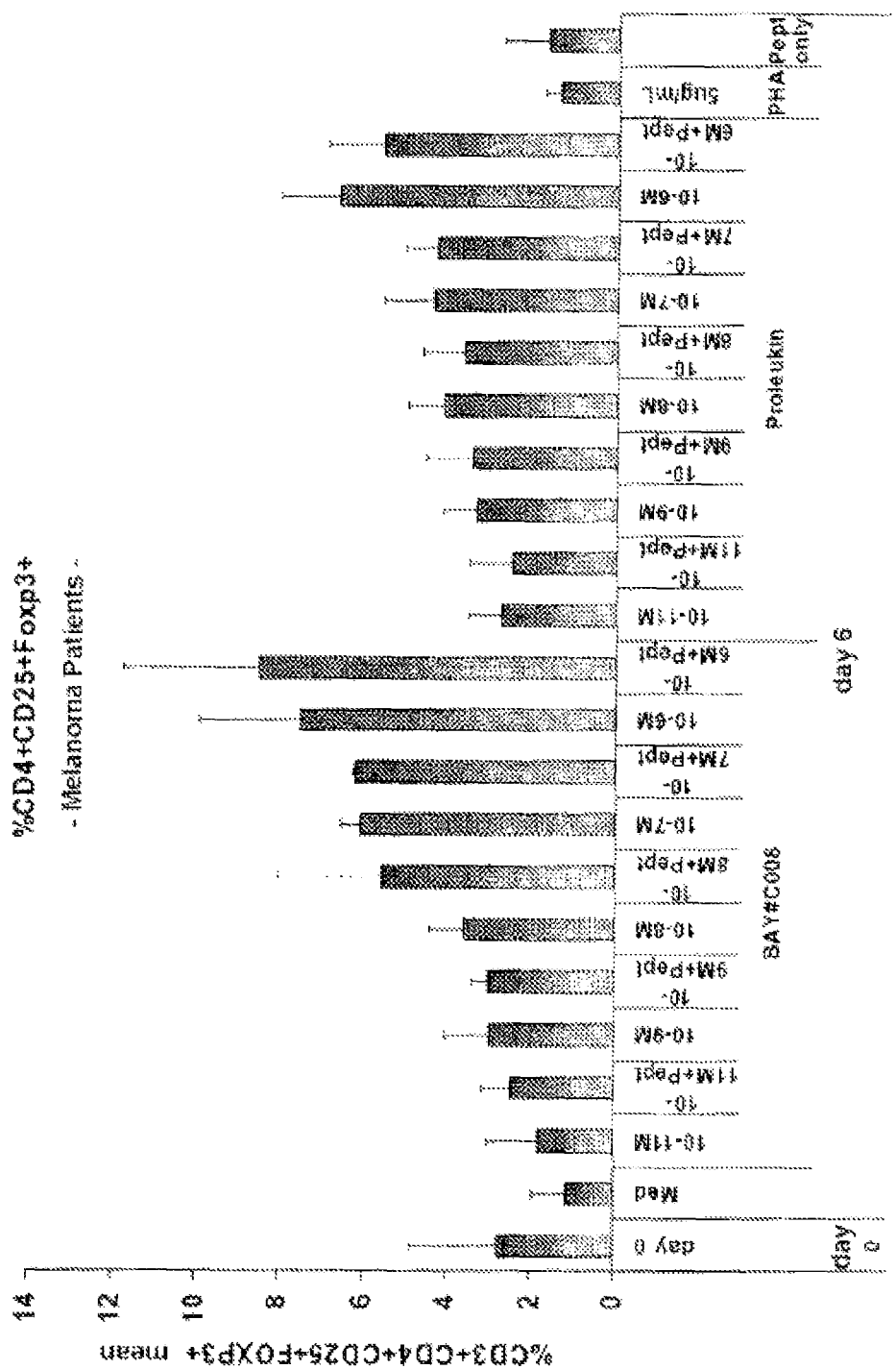
FIG. 3 shows that hIL-2-N88R in melanoma patients at equal or lower dosage in comparison to proleukin induces a greater increase in the regulatory $CD4^+CD25^+Foxp3^+$ T cells.
Figure 4:
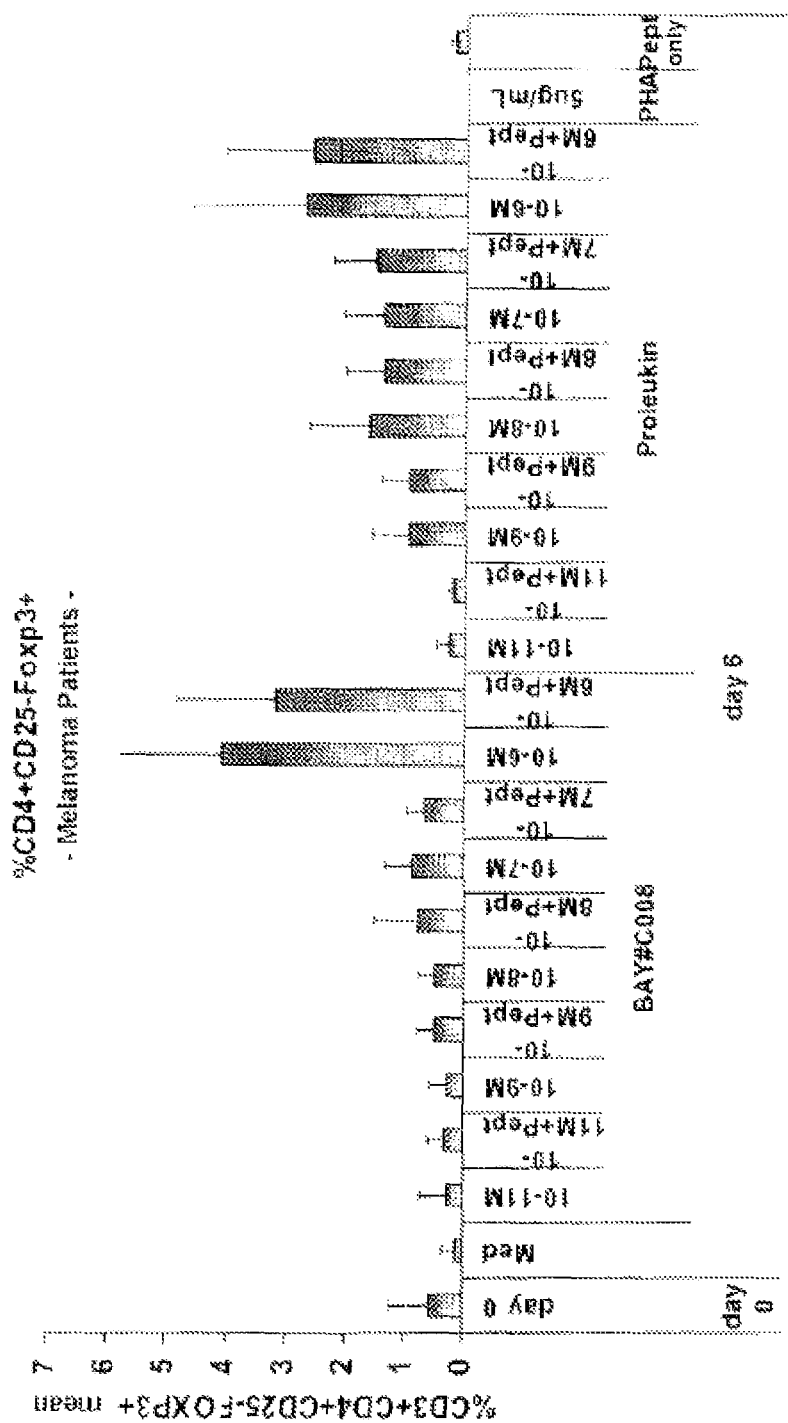
FIG. 4 shows that hIL-2-N88R in melanoma patients at equal or lower dosage in comparison to proleukin induces a greater increase in the regulatory $CD4^+CD25^-Foxp3^+$ T cells.

Next, it was investigated whether the hIL-2 mutein according to the invention N88R also stimulates the antigen-specific activity of immune cells. For this, PBMCs (10$^6$ cells/ml) from three melanoma patients were stimulated with hIL-2-N88R (BAY 50-4798, Lot #PR312C008) or hIL-2 wild type (proleukin) at concentrations which lay between 10$^{-11}$ and 10$^{-6}$ M, in the presence or absence of a melanoma-associated peptide pool, with 5 µg/ml PHA or with culture medium only. Next, the subpopulations of the regulatory T cells CD4$^+$CD25$^+$Foxp3$^+$ and CD4$^+$CD25$^-$Foxp3$^+$ respectively were determined. The result is shown in FIG. 3 and Table 5 and FIG. 4 and Table 6 respectively.

TABLE 5

Percentage of CD3+CD4+CD25+Foxp3+ T cells after stimulation; mean values from three melanoma patients

| | Conditions | | Mean Value | S.D. |
|---|---|---|---|---|
| day 0 | | day 0 | 2.800 | 2.052 |
| day 6 | | Med | 1.133 | 0.839 |
| | hIL-2-N88R | $10^{-11}$M | 1.833 | 1.185 |
| | (BAY #C008) | $10^{-11}$M + Pept | 2.467 | 0.666 |
| | | $10^{-9}$M | 3.000 | 1.015 |
| | | $10^{-9}$M + Pept | 3.033 | 0.379 |
| | | $10^{-8}$M | 3.600 | 0.819 |
| | | $10^{-8}$M + Pept | 5.567 | 2.499 |
| | | $10^{-7}$M | 6.100 | 0.458 |
| | | $10^{-7}$M + Pept | 6.233 | 0.058 |
| | | $10^{-6}$M | 7.533 | 2.413 |
| | | $10^{-6}$M + Pept | 8.533 | 3.225 |
| | hIL-2 wild type | $10^{-11}$M | 2.767 | 0.751 |
| | (proleukin) | $10^{-11}$M + Pept | 2.500 | 0.985 |
| | | $10^{-9}$M | 3.333 | 0.802 |
| | | $10^{-9}$M + Pept | 3.433 | 1.102 |
| | | $10^{-8}$M | 4.133 | 0.862 |
| | | $10^{-8}$M + Pept | 3.633 | 1.002 |
| | | $10^{-7}$M | 4.367 | 1.201 |
| | | $10^{-7}$M + Pept | 4.300 | 0.755 |
| | | $10^{-6}$M | 6.667 | 1.405 |
| | | $10^{-6}$M + Pept | 5.600 | 1.323 |
| | PHA | 5 µg/ml | 1.400 | 0.346 |
| | peptide only | | 1.667 | 1.060 |

TABLE 6

Percentage of CD3+CD4+CD25-Foxp3+ T cells after stimulation; mean values from three melanoma patients

| | Conditions | | Mean Value | S.D. |
|---|---|---|---|---|
| day 0 | | day 0 | 0.567 | 0.643 |
| day 6 | | Med | 0.133 | 0.231 |
| | hIL-2-N88R | $10^{-11}$M | 0.267 | 0.462 |
| | (BAY #C008) | $10^{-11}$M + Pept | 0.333 | 0.252 |
| | | $10^{-9}$M | 0.300 | 0.265 |
| | | $10^{-9}$M + Pept | 0.500 | 0.300 |
| | | $10^{-8}$M | 0.500 | 0.265 |
| | | $10^{-8}$M + Pept | 0.800 | 0.700 |
| | | $10^{-7}$M | 0.900 | 0.436 |
| | | $10^{-7}$M + Pept | 0.677 | 0.306 |
| | | $10^{-6}$M | 4.100 | 1.682 |
| | | $10^{-6}$M + Pept | 3.200 | 1.646 |
| | hIL-2 wild type | $10^{-11}$M | 0.267 | 0.208 |
| | (proleukin) | $10^{-11}$M + Pept | 0.200 | 0.100 |
| | | $10^{-9}$M | 0.967 | 0.603 |
| | | $10^{-9}$M + Pept | 0.967 | 0.451 |
| | | $10^{-8}$M | 1.633 | 1.002 |
| | | $10^{-8}$M + Pept | 1.400 | 0.624 |
| | | $10^{-7}$M | 1.400 | 0.656 |
| | | $10^{-7}$M + Pept | 1.533 | 0.702 |
| | | $10^{-6}$M | 2.733 | 1.861 |
| | | $10^{-6}$M + Pept | 2.600 | 1.473 |
| | PHA | 5 µg/ml | 0.000 | 0.000 |
| | peptide only | | 0.200 | 0.100 |

Here it was found that the administration of hIL-2-88R also leads to a marked increase in the regulatory T cells in melanoma patients. In the case of the subpopulation CD4+CD25+Foxp3+ at concentrations of $10^{-7}$ M and $10^{-6}$ M, and in the subpopulation CD4+CD25-Foxp3+ at a concentration of $10^{-6}$ M, this is markedly greater than with stimulation with corresponding concentrations of wild type-IL-2 (proleukin).

2.3 hIL-2-N88R Induces Regulatory T Cells in Patients with Multiple Sclerosis

Figure 5:
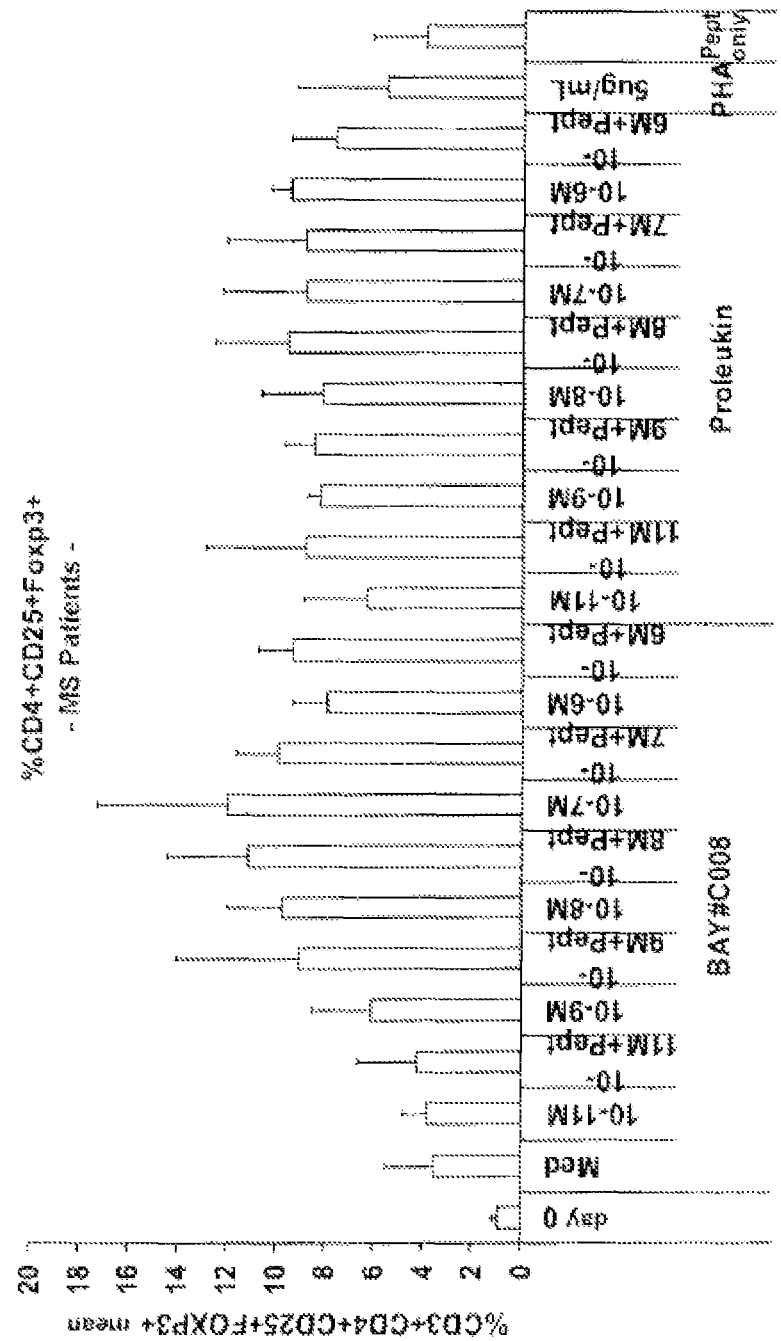
FIG. 5 shows that hIL-2-N88R in multiple sclerosis patients at equal or lower dosage in comparison to proleukin induces a greater increase in the regulatory CD4$^+$CD25$^+$ Foxp3$^+$ T cells.
Figure 6:
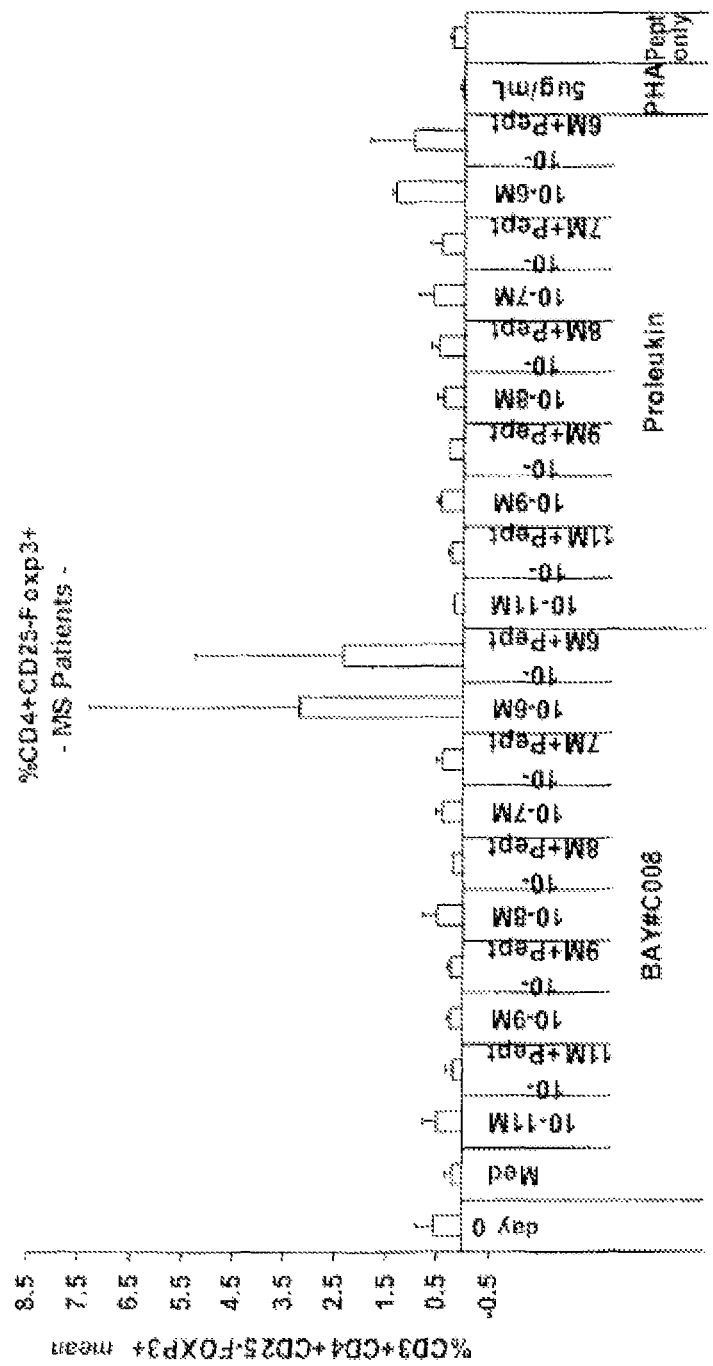
FIG. 6 shows that hIL-2-N88R in multiple sclerosis patients at equal or lower dosage in comparison to proleukin induces a greater increase in the regulatory CD4$^+$CD25$^-$ Foxp3$^+$ T cells.

Next it was investigated whether the hIL-2 mutein according to the invention N88R also stimulates the antigen-specific activity of immune cells. For this, PBMCs ($10^6$ cells/ml) from two multiple sclerosis patients were stimulated with hIL-2-N88R (BAY 50-4798, Lot #PR312C008) or hIL-2 wild type (proleukin) at concentrations which lay between $10^{-11}$ and $10^{-6}$ M, in the presence or absence of a multiple sclerosis-associated peptide, with 5 µg/ml PHA or with culture medium only. Next, the subpopulations of the regulatory T cells CD4+CD25+Foxp3+ and CD4+CD25-Foxp3+ respectively were determined. The result is shown in FIG. 5 and Table 7 and FIG. 6 and Table 8 respectively.

TABLE 7

Percentage of CD3+CD4+CD25+Foxp3+ T cells after stimulation; mean values from two multiple sclerosis patients.

| | Conditions | | Mean Value | S.D. |
|---|---|---|---|---|
| day 0 | | day 0 | 0.95 | 0.21 |
| day 6 | | Med | 3.55 | 1.91 |
| | hIL-2-N88R | $10^{-11}$M | 3.8 | 0.99 |
| | (BAY #C008) | $10^{-11}$M + Pept | 4.2 | 2.40 |
| | | $10^{-9}$M | 6.1 | 2.40 |
| | | $10^{-9}$M + Pept | 9.05 | 5.02 |
| | | $10^{-8}$M | 9.75 | 2.19 |
| | | $10^{-8}$M + Pept | 11.15 | 3.32 |
| | | $10^{-7}$M | 11.95 | 5.30 |
| | | $10^{-7}$M + Pept | 9.9 | 1.70 |
| | | $10^{-6}$M | 7.9 | 1.41 |
| | | $10^{-6}$M + Pept | 9.3 | 1.41 |
| | hIL-2 wild type | $10^{-11}$M | 6.3 | 2.55 |
| | (proleukin) | $10^{-11}$M + Pept | 8.8 | 4.10 |
| | | $10^{-9}$M | 8.25 | 0.49 |
| | | $10^{-9}$M + Pept | 8.45 | 1.20 |
| | | $10^{-8}$M | 8.15 | 2.47 |
| | | $10^{-8}$M + Pept | 9.55 | 3.04 |
| | | $10^{-7}$M | 8.8 | 3.39 |
| | | $10^{-7}$M + Pept | 8.8 | 3.25 |
| | | $10^{-6}$M | 9.45 | 0.78 |
| | | $10^{-6}$M + Pept | 7.6 | 1.84 |
| | PHA | 5 µg/ml | 5.5 | 3.68 |
| | peptide only | | 3.95 | 2.19 |

TABLE 8

Percentage of CD3+CD4+CD25-Foxp3+ T cells after stimulation; mean values from two multiple sclerosis patients

| | Conditions | | Mean Value | S.D. |
|---|---|---|---|---|
| day 0 | | day 0 | 0.35 | 0.35 |
| day 6 | | Med | 0.14 | 0.14 |
| | hIL-2-N88R | $10^{-11}$M | 0.28 | 0.28 |
| | (BAY #C008) | $10^{-11}$M + Pept | 0.14 | 0.14 |
| | | $10^{-9}$M | 0.07 | 0.07 |
| | | $10^{-9}$M + Pept | 0.07 | 0.07 |
| | | $10^{-8}$M | 0.28 | 0.28 |
| | | $10^{-8}$M + Pept | 0.00 | 0.00 |
| | | $10^{-7}$M | 0.14 | 0.14 |
| | | $10^{-7}$M + Pept | 0.14 | 0.14 |
| | | $10^{-6}$M | 4.10 | 4.10 |
| | | $10^{-6}$M + Pept | 2.90 | 2.90 |
| | hIL-2 wild type | $10^{-11}$M | 0.00 | 0.00 |
| | (proleukin) | $10^{-11}$M + Pept | 0.07 | 0.07 |
| | | $10^{-9}$M | 0.07 | 0.07 |
| | | $10^{-9}$M + Pept | 0.00 | 0.00 |
| | | $10^{-8}$M | 0.14 | 0.14 |
| | | $10^{-8}$M + Pept | 0.14 | 0.14 |
| | | $10^{-7}$M | 0.28 | 0.28 |
| | | $10^{-7}$M + Pept | 0.21 | 0.21 |
| | | $10^{-6}$M | 0.07 | 0.07 |
| | | $10^{-6}$M + Pept | 0.85 | 0.85 |
| | PHA | 5 µg/ml | 0.07 | 0.07 |
| | peptide only | | 0.07 | 0.07 |

It was found that the administration of hIL-2-N88R also leads to a marked increase in the T cells in multiple sclerosis patients. In the case of the subpopulation CD4+CD25+

Foxp3+ at concentrations of $10^{-8}$ M and $10^{-7}$ M, and in the subpopulation CD4+CD25−Foxp3+ at a concentration of $10^{-6}$ M, this is markedly greater than with stimulation with corresponding concentrations of hIL-2 wild type (proleukin).

Figure 7:
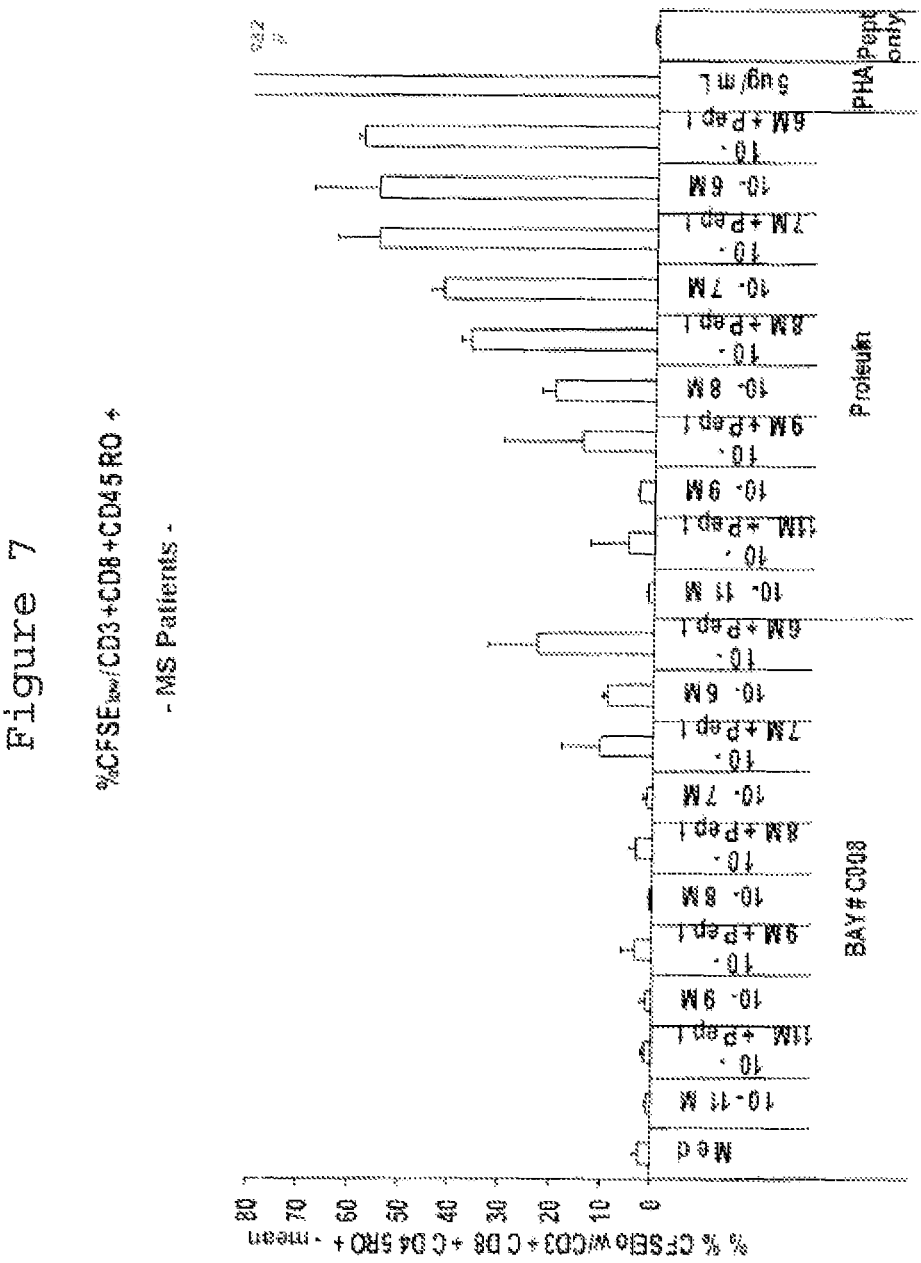
FIG. 7 shows that hIL-2-N88R in multiple sclerosis patients at equal or higher dosage in comparison to proleukin induces a lower increase in the cytotoxic CFSElow/CD3$^+$CD8$^+$CD45RO$^+$ T cells.
Figure 8:
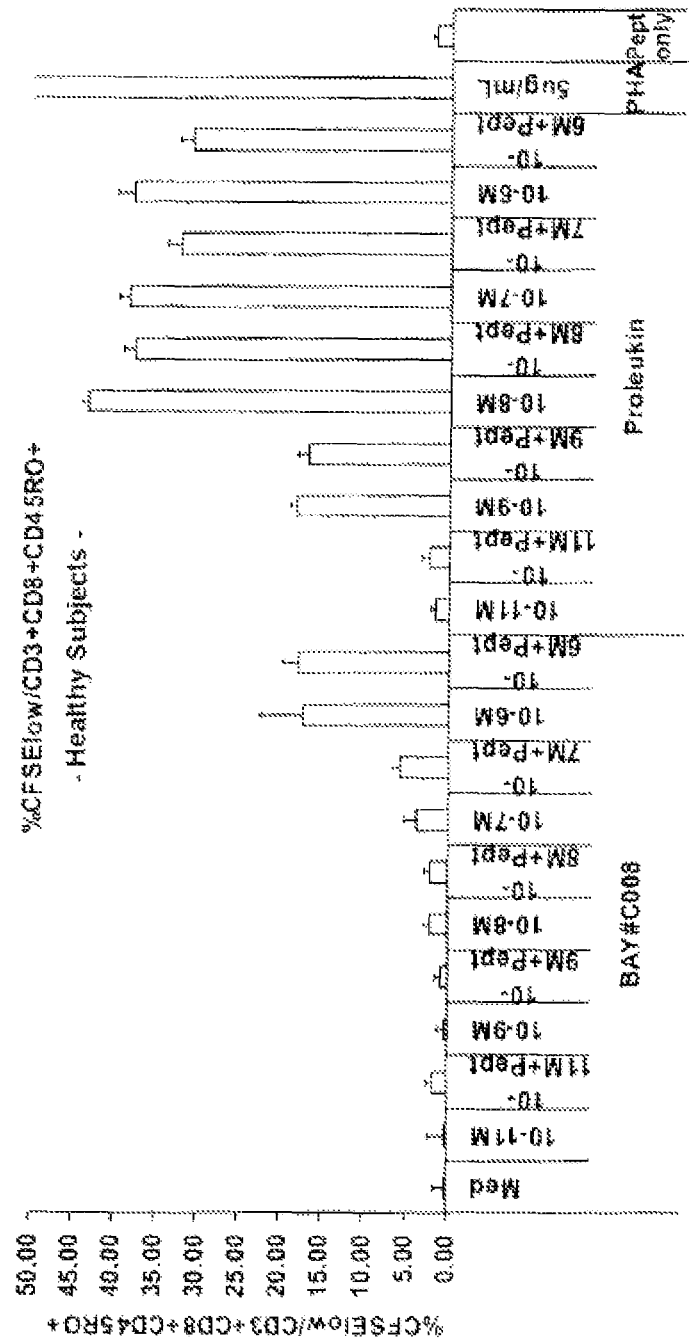
FIG. 8 shows that hIL-2-N88R in healthy subjects at equal or higher dosage in comparison to proleukin induces a lower increase in the cytotoxic CFSElow/CD3$^+$CD8$^+$CD45RO$^+$ T cells.

2.4 hIL-2-N88R Induces Only Minimal Proliferation of Cytotoxic CD8+ T Cells in Patients with Multiple Sclerosis and in Healthy Subjects Further, the stimulation of cytotoxic CD8+ central memory T cells was studied. For this, PBMCs from healthy subjects or multiple sclerosis patients were treated as described in 2.3. The percentage of CFSElow/CD3+CD8+CD45RO+ T cells was analysed. The result is shown in FIG. 7 and Table 9 and FIG. 8 and Table 10.

TABLE 9

Percentage of CFSElow/CD3+CD8+CD45RO+ T cells after stimulation; mean values from two multiple sclerosis patients.

| | Conditions | Mean Value | S.D. |
|---|---|---|---|
| day 0 | day 0 | 2.45 | 1.06 |
| day 6 | Med | 0.95 | 0.21 |
| hIL-2-N88R | $10^{-11}$M | 1.3 | 0.57 |
| (BAY #C008) | $10^{-11}$M + Pept | 1.2 | 1.13 |
| | $10^{-9}$M | 3.55 | 2.47 |
| | $10^{-9}$M + Pept | 0.5 | 0.14 |
| | $10^{-8}$M | 3.3 | 1.41 |
| | $10^{-8}$M + Pept | 1.2 | 0.71 |
| | $10^{-7}$M | 10.5 | 7.50 |
| | $10^{-7}$M + Pept | 9.1 | 0.71 |
| | $10^{-6}$M | 22.9 | 9.76 |
| | $10^{-6}$M + Pept | 1 | 0.28 |
| hIL-2 wild type | $10^{-11}$M | 5.2 | 7.35 |
| (proleukin) | $10^{-11}$M + Pept | 3.1 | 0.28 |
| | $10^{-9}$M | 14.3 | 15.56 |
| | $10^{-9}$M + Pept | 19.45 | 2.90 |
| | $10^{-8}$M | 36.5 | 1.98 |
| | $10^{-8}$M + Pept | 41.85 | 2.47 |
| | $10^{-7}$M | 54.8 | 8.49 |
| | $10^{-7}$M + Pept | 54.85 | 12.94 |
| | $10^{-6}$M | 58.05 | 1.06 |
| | $10^{-6}$M + Pept | 98.2 | 0.85 |
| PHA | 5 µg/ml | 0.55 | 0.07 |
| peptide only | | 2.45 | 1.06 |

TABLE 10

Percentage of CFSElow/CD3+CD8+CD45RO+ T cells after stimulation; mean values from three healthy subjects

| | Conditions | Mean Value | S.D. |
|---|---|---|---|
| day 6 | Med | 0.23 | 0.23 |
| hIL-2-N88R | $10^{-11}$M | 0.27 | 0.06 |
| (BAY #C008) | $10^{-11}$M + Pept | 1.73 | 2.23 |
| | $10^{-9}$M | 0.43 | 0.23 |
| | $10^{-9}$M + Pept | 0.80 | 0.72 |
| | $10^{-8}$M | 2.13 | 1.86 |
| | $10^{-8}$M + Pept | 2.07 | 1.17 |
| | $10^{-7}$M | 3.83 | 4.02 |
| | $10^{-7}$M + Pept | 5.77 | 6.30 |
| | $10^{-6}$M | 17.43 | 17.31 |
| | $10^{-6}$M + Pept | 17.87 | 12.97 |
| hIL-2 wild type | $10^{-11}$M | 1.53 | 1.23 |
| (proleukin) | $10^{-11}$M + Pept | 2.37 | 2.57 |
| | $10^{-9}$M | 18.20 | 23.35 |
| | $10^{-9}$M + Pept | 16.93 | 10.96 |
| | $10^{-8}$M | 43.30 | 36.72 |
| | $10^{-8}$M + Pept | 37.80 | 20.80 |
| | $10^{-7}$M | 38.53 | 25.53 |
| | $10^{-7}$M + Pept | 32.37 | 20.90 |
| | $10^{-6}$M | 37.93 | 27.66 |
| | $10^{-6}$M + Pept | 30.83 | 21.51 |
| PHA | 5 µg/ml | 96.07 | 1.79 |
| peptide only | | 1.83 | 1.59 |

In contrast to hIL-2 wild type, in multiple sclerosis patients and also in healthy subjects, hIL-2-N88R leads to only a slight proliferation of central memory CD8+ T cells, and this at every concentration studied.

Figure 9:
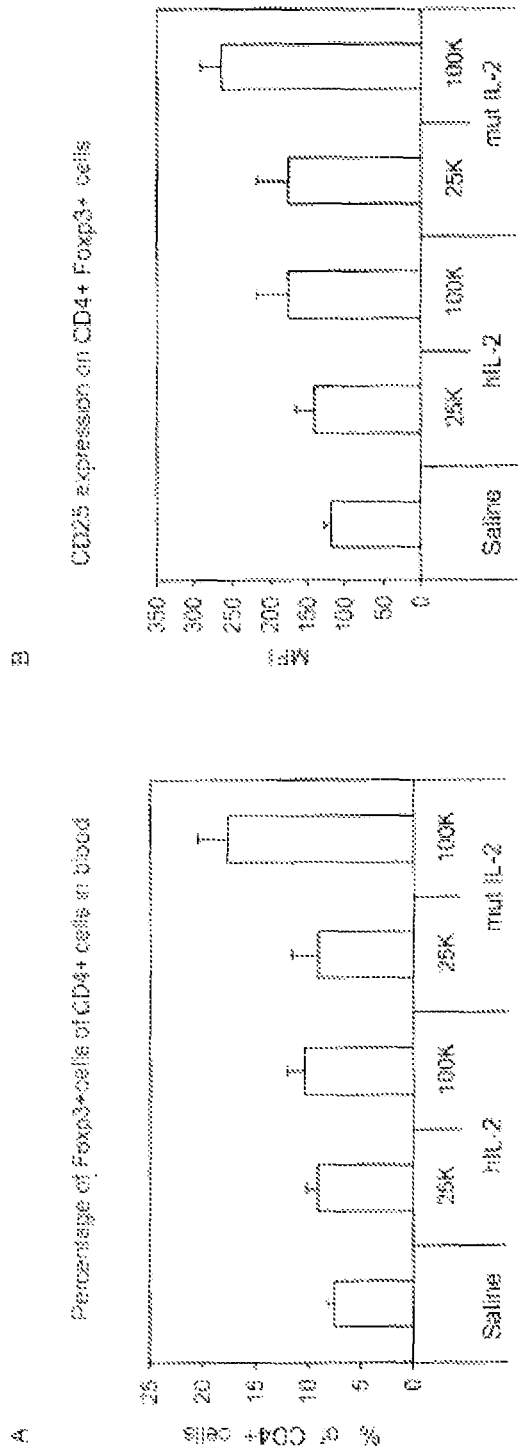
FIG. 9 shows that hIL-2-N88R in the mouse type I diabetes model in comparison to hIL-2 wild type leads to a higher percentage increase in FoxP3$^+$ cells within the CD4$^+$ cells (A). In addition, these CD4$^+$FoxP3$^+$ cells exhibit higher expression of CD25 (B).
Figure 10:
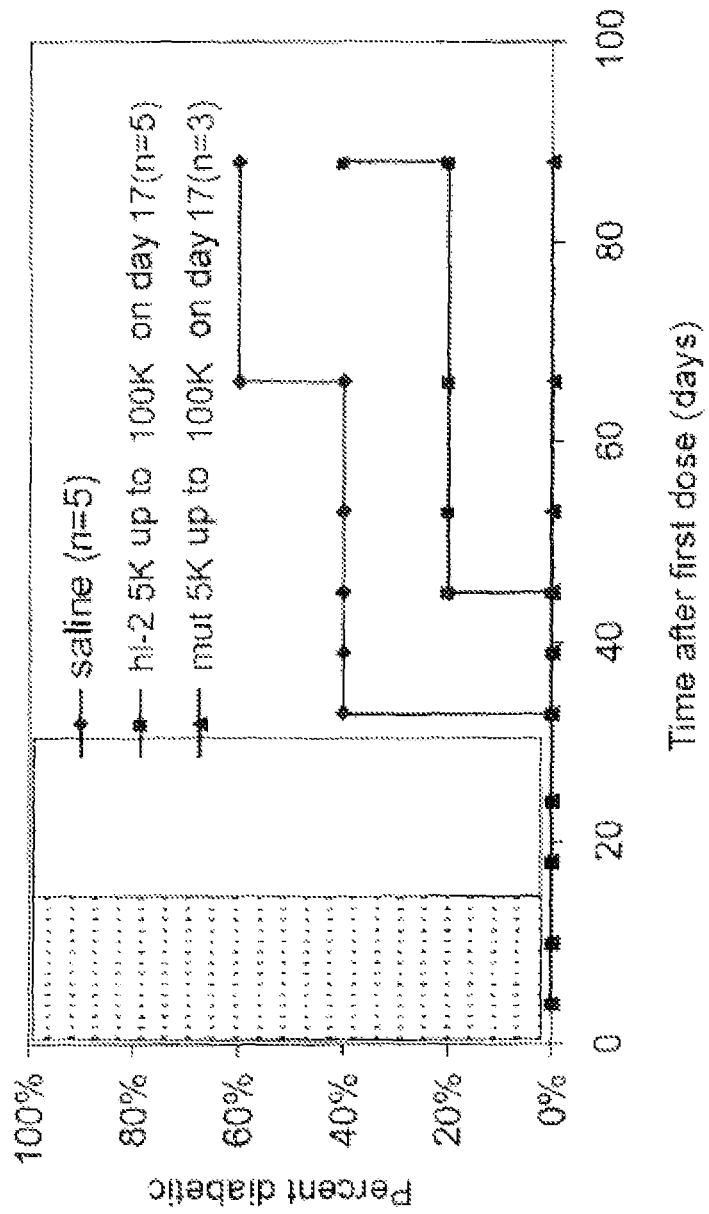
FIG. 10 shows that in the mouse type I diabetes model, in contrast to hIL-2 wild type, hIL-2-N88R prevents the development of diabetes.

2.5 Treatment with hIL-2 Mutein Prevents the Development of Type I Diabetes in the Animal Model In comparison to hIL-2 wild type, the treatment of NOD mice with hIL-2-N88R leads to a higher percentage increase in FoxP3+ cells within the CD4+ cells (FIG. 9 (A)). In addition, these CD4+FoxP3+ positive cells exhibit higher expression of CD25 (FIG. 9 (B)). FIG. 10 shows that, in contrast to the hIL-2 wild type, hIL-2-N88R treatment in the mouse type I diabetes model prevents the development of the diabetes in all mice in the treatment group.

3. Conclusion

The experiments performed by the inventors show clearly that owing to their potential for the induction of regulatory T cells ($T_{Reg}$) the hIL-2 muteins according to the invention and sections thereof are substances which are suitable for the treatment and/or prophylaxis of an autoimmune disease or for the induction of $T_{Reg}$ in an organism and for the formation of $T_{Reg}$ in vitro. This is demonstrated by the inventors not only in vitro but also in vivo.

The invention claimed is:

1. A method for the treatment and/or prevention of the worsening of an autoimmune disease in an organism, the method comprising:
   (a) administering a mutein of human interleukin-2 (hIL-2 mutein) to the organism, wherein said hIL-2 mutein has an amino acid substitution in at least one of the positions 20, 88 or 126, numbered in accordance with the hIL-2 wild type sequence as set forth in SEQ ID NO: 1; and
   (b) if necessary, repeating step (a),
   wherein the autoimmune disease is type I diabetes, multiple sclerosis, or systemic lupus erythematosus, and wherein the administration induces regulatory T cells in the organism.

2. The method according to claim 1, wherein through the substitution at position 88 an asparagine is exchanged for an amino acid which is selected from the group consisting of: arginine (hIL-2-N88R), glycine (hIL-2-N88G), or isoleucine (hIL-2-N88I).

3. The method according to claim 1, wherein through the substitution at position 20 an aspartic acid is exchanged for an amino acid which is selected from the group consisting of: histidine (hIL-2-D20H), isoleucine (hIL-2-D20I), or tyrosine (hIL-2-D20Y).

4. The method according to claim 1, wherein through the substitution at position 126, a glutamine is exchanged for a leucine (hIL-2-Q126L).

5. The method according to claim 1, wherein the method further comprises administering to the organism an immunosuppressant.

6. The method according to claim 5, wherein the immunosuppressant is selected from the group consisting of: glucocorticoid, including decortin, prednisol; azathioprine; cyclosporin A; tacrolimus; an anti-T lymphocyte globulin; an anti-CD3 antibody; muromonab; an anti-CD25 antibody; basiliximab; daclizumab; an anti-TNF-α antibody; infliximab; adalimumab; azathioprine; methotrexate; cyclosporin; sirolimus; everolimus; fingolimod; CELLCEPT® (mycophenolate mofetil); myfortic; and cyclophosphamide.

7. The method according to claim 1, wherein the autoimmune disease is type I diabetes.

8. The method according to claim 1, wherein the autoimmune disease is multiple sclerosis.

9. The method according to claim 1, wherein the autoimmune disease is systemic lupus erythematosus (SLE).

10. A method for the treatment and/or prevention of the worsening of an autoimmune disease in an organism, the method comprising:
    (a) administering a mutein of human interleukin-2 (hIL-2 mutein) to the organism, wherein said hIL-2 mutein has an amino acid substitution in at least one of the positions 20, 88 or 126, numbered in accordance with the hIL-2 wild type sequence as set forth in SEQ ID NO: 1; and
    (b) if necessary, repeating step (a),
    wherein the autoimmune disease is type I diabetes or multiple sclerosis.

11. The method according to claim 10, wherein through the substitution at position 88 an asparagine is exchanged for an amino acid which is selected from the group consisting of: arginine (hIL-2-N88R), glycine (hIL-2-N88G), or isoleucine (hIL-2-N88I).

12. The method according to claim 10, wherein through the substitution at position 20 an aspartic acid is exchanged for an amino acid which is selected from the group consisting of: histidine (hIL-2-D20H), isoleucine (hIL-2-D20I), or tyrosine (hIL-2-D20Y).

13. The method according to claim 10, wherein through the substitution at position 126, a glutamine is exchanged for a leucine (hIL-2-Q126L).

14. The method according to claim 10, wherein the method further comprises administering to the organism an immunosuppressant.

15. The method according to claim 14, wherein the immunosuppressant is selected from the group consisting of: glucocorticoid; decortin; prednisol; azathioprine; cyclosporin A; tacrolimus; an anti-T lymphocyte globulin; an anti-CD3 antibody; muromonab; an anti-CD25 antibody; basiliximab; daclizumab; an anti-TNF-α antibody; infliximab; adalimumab; azathioprine; methotrexate; cyclosporin; sirolimus; everolimus; fingolimod; CELLCEPT® (mycophenolate mofetil); myfortic; and cyclophosphamide.

* * * * *